(12) United States Patent
Thies et al.

(10) Patent No.: US 9,370,510 B2
(45) Date of Patent: Jun. 21, 2016

(54) SMALL MOLECULE COMPOUNDS TO TREAT HEARING LOSS

(71) Applicant: FATE THERAPEUTICS, INC., San Diego, CA (US)

(72) Inventors: Robert Scott Thies, San Diego, CA (US); Francine Farouz, San Carlos, CA (US); Zhiyong Wang, San Diego, CA (US); Chin-Chun Jean Lu, San Diego, CA (US)

(73) Assignee: Fate Therapeutics, Inc., San Diego, CA (US)

( * ) Notice: Subject to any disclaimer, the term of this patent is extended or adjusted under 35 U.S.C. 154(b) by 0 days.

(21) Appl. No.: 14/380,669

(22) PCT Filed: Feb. 22, 2013

(86) PCT No.: PCT/US2013/027471
§ 371 (c)(1),
(2) Date: Aug. 22, 2014

(87) PCT Pub. No.: WO2013/126805
PCT Pub. Date: Aug. 29, 2013

(65) Prior Publication Data
US 2015/0025096 A1 Jan. 22, 2015

Related U.S. Application Data

(60) Provisional application No. 61/603,125, filed on Feb. 24, 2012.

(51) Int. Cl.
| | | |
|---|---|---|
| A01N 43/38 | (2006.01) |
| A61K 31/40 | (2006.01) |
| A61K 31/475 | (2006.01) |
| A61K 31/404 | (2006.01) |
| A61K 31/506 | (2006.01) |
| A61K 31/55 | (2006.01) |
| A61K 9/00 | (2006.01) |

(52) U.S. Cl.
CPC ............. *A61K 31/475* (2013.01); *A61K 9/0046* (2013.01); *A61K 31/404* (2013.01); *A61K 31/506* (2013.01); *A61K 31/55* (2013.01)

(58) Field of Classification Search
None
See application file for complete search history.

(56) References Cited

U.S. PATENT DOCUMENTS

| | | | |
|---|---|---|---|
| 5,421,818 A | 6/1995 | Arenberg |
| 5,474,529 A | 12/1995 | Arenberg |
| 5,476,446 A | 12/1995 | Arenburg |
| 6,045,528 A | 4/2000 | Arenberg et al. |
| 8,870,826 B2 | 10/2014 | Reed et al. |

FOREIGN PATENT DOCUMENTS

WO   WO 2013/126805 A2   8/2013

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Adam et al., "Cell fate choices and the expression of Notch, Delta and Serrate homologues in the chick inner ear: parallels with *Drosophila* sense-organ development", Dev., 125: 4645-4654 (1998).
Brigande and Heller, "Quo vadis, hair cell regeneration?", Nat Neurosci., 12(6): 679-685 (2009). doi:10.1038/nn.2311. Epub May 26, 2009.
Chen & Segil, "p27(Kip1) links cell proliferation to morphogenesis in the developing organ of Corti", Development, 126(8): 1581-1590 (1999).
Chen et al., "Progressive hearing loss in mice lacking the cyclin-dependent kinase inhibitor Ink4d", Nat Cell Biol., 5: 422-426 (2003).
Corwin and Cotanche, "Regeneration of Sensory Hair Cells After Acoustic Trauma", Science, 240: 1772-1774 (1988).
Cotanche, "Regeneration of hair cell stereociliary bundles in the chick cochlea following severe acoustic trauma", Hearing Research, 30: 181-196 (1987).
Cruz et al., "Light Microscopic Evidence of Hair Cell Regeneration After Gentamicin Toxicity in Chick Cochlea", Arch Otolaryngol Head Neck Surg., 113: 1058-1062 (1987).
Daudet and Lewis, "Two contrasting roles for Notch activity in chick inner ear development: specification of prosensory patches and lateral inhibition of hair-cell differentiation", Dev., 132: 541-551 (2005).
Duncan et al., "Differential Expression of Unconventional Myosins in Apoptotic and Regenerating Chick Hair Cells Confirms Two Regeneration Mechanisms", Journal of Comparative Neurology, 499: 691-701 (2006).
Fekete and Wu, "Revisiting cell fate specification in the inner ear", Curr Opin Neurobiol., 12:35-42 (2002).
Gray's Anatomy, Revised American Edition (1977), pp. 859-867.
International Search Report and Written Report in International Application No. PCT/US2013/027471 dated Jun. 25, 2013, 6 pages.
International Preliminary Report on Patentability in International Application No. PCT/US2013/027471 dated Aug. 26, 2014, 5 pages.
Jurayj et al., "Design and synthesis of ellipticinium salts and 1,2-dihydroellipticines with high selectivities against human CNS cancers in vitro", J. Med. Chem., 37: 2190-2197 (1994).
Lee & Cotanche, "Detection of β-actin mRNA by RT-PCR in normal and regenerating chicken cochleae", Hear Res., 87: 9-15 (1995).
Lee & Cotanche, "Potential role of bFGF and retinoic acid in the regeneration of chicken cochlear hair cells", Hear Res., 94: 1-13 (1996).
Lewis, "Rules for the production of sensory cells", Ciba Foundation Symposia, 160: 25-39 (1991).
Lippe et al., "Hair cell regeneration in the chicken cochlea following aminoglycoside toxicity", Hearing Research, 56: 203-210 (1991).

(Continued)

*Primary Examiner* — Jeffrey H Murray
(74) *Attorney, Agent, or Firm* — Cooley LLP

(57) ABSTRACT

The invention is directed, in part, to compositions comprising small molecule compounds to treat or prevent hearing loss. Compositions of the present invention also promote sensory hair cell regeneration. Particular compositions comprise ellipticine derivatives, and optionally one or more small molecules that increase Atoh1 expression or activity, and optionally one or more growth factors.

22 Claims, 4 Drawing Sheets

(56) References Cited

OTHER PUBLICATIONS

Lowenheim et al., "Gene disruption of p27$^{Kip1}$ allows cell proliferation in the postnatal and adult organ of Corti", Proc Natl Acad Sci USA., 96: 4084-4088 (1999).

Mantela et al. "The retinoblastoma gene pathway regulates the postmitotic state of hair cells of the mouse inner ear", Development, 132: 2377-2388 (2005).

Minoda et al., "Manipulating cell cycle regulation in the mature cochlea", Hear Res., 232: 44-51 (2007).

Oesterle et al., p27$^{Kip1}$ is required to maintain proliferative quiescence in the adult cochlea and pituitary, Cell Cycle, 10(8):1-12 (2011).

Roberson et al., "Direct Transdifferentiation Gives Rise to the Earliest New Hair Cells in Regenerating Avian Auditory Epithelium", Journal of Neuroscience Research, 78: 461-471 (2004).

Ruben, "Development of the Inner Ear of the Mouse: A Radioautographic Study of Terminal Mitoses", Acta Otolaryngol Suppl., 220: 1-44 (1967).

Ryals and Rubel, "Hair Cell Regeneration After Acoustic Trauma in Adult Coturix Quail", Science, 240: 1774-1776 (1988).

Sage et al., "Essential role of retinoblastoma protein in mammalian hair cell development and hearing", PNAS, 103: 7345-7350 (2006).

Sage et al., "Proliferation of functional hair cells in vivo in the absence of the retinoblastoma protein", Science, 307: 1114-1118 (2005).

Stone and Rubel, "Delta1 expression during avian hair cell regeneration", Dev., 126: 961-973 (1999).

* cited by examiner

| Number | Compound | Structure |
|---|---|---|
| 1 | 2(N)methyl ellipticine | 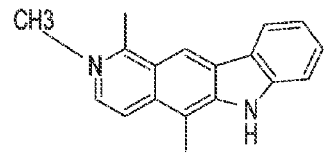 |
| 2 | 2(N)methyl olivacine | 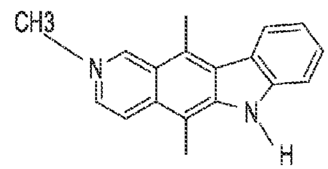 |
| 3 | 2(N)benzyl ellipticine | 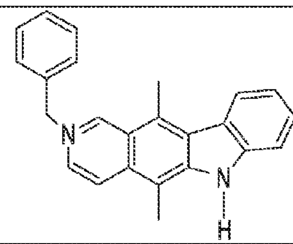 |
| 4 | 2(N)methylacetate ellipticine | 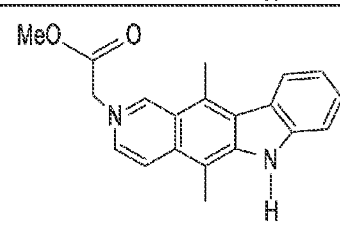 |
| 5 | 2(N)methyl methyl ether ellipticine | 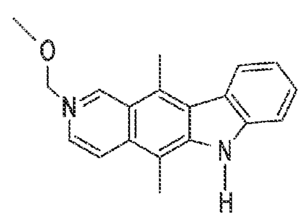 |

SMALL MOLECULE COMPOUNDS TO TREAT HEARING LOSS

CROSS-REFERENCE TO RELATED APPLICATIONS

This application is a §371 U.S. national stage entry of international application no. PCT/US2013/027471, filed Feb. 22, 2013, which application claims the benefit under 35 U.S.C. §119(e) of U.S. Provisional Application No. 61/603,125, filed Feb. 24, 2012, each of which is incorporated herein by reference in its entirety.

BACKGROUND

1. Technical Field

The present invention relates generally to methods to improve hearing in subjects. More particularly, the present invention relates to the use of novel compositions to promote partial or complete restoration of hearing in a subject.

2. Description of the Related Art

Millions of people are debilitated by hearing loss: almost 49 million people in the US and over 249 million worldwide suffer from hearing impairments (Cotanche and Kaiser, *Hear Res.* 266(1-2): 18-25 (2010)). The frequency and severity of hearing loss increases with age: 17% of children under age 18, 30% of people over 65, and over 90% of people over 80 have a substantial hearing loss. Id. Although rarely life-threatening, hearing loss affects more people than epilepsy, multiple sclerosis, spinal injury, stroke, Huntington's and Parkinson's diseases combined and has a huge financial impact on our economy and lifestyle (Hudspeth, *Neuron.* 19: 947-950, (1997)).

Hearing impairment is mainly caused by damage to the cochlear hair cells, the sensory cells in the cochlea. Cochlear hair cell damage can result from a number of causes, including age-related damage or loss (presbycusis), noise exposure, drug exposure, e.g., aminoglycoside antibiotics and anti-cancer therapeutics, infections, syndromic and non-syndromic genetic mutations, and autoimmune disease.

In mammals, loss of cochlear hair cells results in permanent hearing loss because they are generated only during embryonic development and do not regenerate during one's lifetime (Ruben, *Acta Otolaryngol Suppl.* 220:1-44, (1967)). Avians however, have the ability to regenerate cochlear hair cells throughout their lifetime (Cotanche, *Hear Res.* 30: 181-196, (1987); Cruz et al., *Arch Otolaryngol Head Neck Surg.* 113: 1058-1062, (1987); Corwin and Cotanche, *Science.* 240: 1772-1774, (1988); Ryals and Rubel, *Science.* 240: 1774-1776, (1988); Lippe et al., *Hear Res.* 56: 203-210, (1991)). Cochlear hair cell regeneration in avians is not merely a delayed developmental response, as six-year-old quails (which is three years beyond their average lifespan) can regenerate hair cells as readily as newborn chicks (Ryals and Rubel, 1988).

Currently, treatments for hearing loss include electronic cochlear implants, hearing assistive technology, audiologic rehabilitation, and the use of hearing aids. All of these treatment modalities have relatively limited therapeutic potential and more importantly, do not address the problem of restoring cochlear structure and function. However, attempts to restore cochlear structure and function in the mammalian cochlea have been disappointing, at best. In fact, to date, no clinically acceptable treatments exist for regeneration of the human cochlea to treat or prevent hearing loss.

Thus, while cochlear hair cell regeneration offers the promise of a therapeutic treatment for sensorineural hearing loss in humans, this promise is far from being realized. Accordingly, there is a substantial long-felt, but unmet, need in the art for therapeutic compositions and methods that promote mammalian hair cell regeneration. The present invention offers solutions to these and other problems vexing the art.

BRIEF SUMMARY

The present invention provides compositions comprising small molecule compounds, e.g., ellipticine derivatives, to treat or prevent hearing loss. The ellipticine derivatives are normally cytotoxic and used in cancer therapy regimens. The inventors surprisingly and unexpectedly found that ellipticine derivatives are useful for restoring hearing and/or balance in a subject by promoting or increasing, for example, sensory hair cell regeneration. In particular embodiments, compositions comprising ellipticine derivatives, and optionally one or more small molecules that induces or increases Atoh 1 gene and/or protein expression and/or activity of Atoh 1 protein, increase or promote cochlear support cell proliferation and/or dedifferentiation, subsequent differentiation of the proliferated and/or dedifferentiated support cells into sensory hair cells, and cochlear support cell transdifferentiation to sensory hair cells, compared to control or vehicle compositions.

In various embodiments, the invention contemplates, in part, a method for promoting sensory hair cell regeneration comprising administering to a subject, a composition comprising an ellipticine derivative in an amount effective to increase sensory hair cells in the subject, thereby promoting sensory hair cell regeneration in the subject.

In one embodiment, the subject has a partial or complete loss of hearing or balance.

In a particular embodiment, the subject has sensorineural hearing loss due to acute or chronic exposure to ototoxic compounds, acute or chronic exposure to noise, age related hearing loss, a genetic related hearing loss, or has auditory neuropathy.

In a certain embodiment, the subject is at risk of developing sensorineural hearing loss or auditory neuropathy.

In an additional embodiment, the ellipticine derivative is a compound of Structure I:

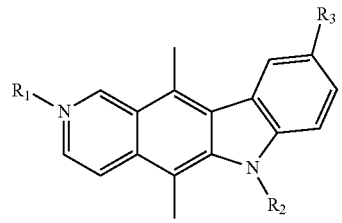

wherein $R_1$ is hydrogen, alkyl, cycloalkyl, cycloalkylalkyl, aryl, aralkyl, heterocyclyl, heterocyclylalkyl, heteroaryl or heteroarylalkyl, wherein $R_1$ is optionally substituted with one or more $R_4$; $R_2$ is, independently, hydrogen, alkyl, haloalkyl, —CN, —C(=O)NR$_5$R$_6$, —C(=O)OR$_5$, —SO$_2$R$_5$, -aryl or heteroaryl, wherein each $R_2$ is optionally substituted with one or more $R_4$; $R_3$ is, independently, hydrogen, halogen, alkyl, haloalkyl, —OR$_5$, —CN, —N$_3$, —NR$_5$R$_6$, —C(=O)NR$_5$R$_6$, —NR$_5$C(=O)R$_6$, —C(=O)OR$_6$, —SR$_5$, —SOR$_5$ and —SO$_2$R$_5$; NR$_5$C(=O)OR$_6$, —NR$_5$C(=O)NR$_5$R$_6$, —O(C=O)R$_5$, —NR$_5$SO$_2$R$_6$, aryl or heteroaryl; each $R_4$, is independently, hydrogen, alkyl, cycloalkyl, aryl, heterocyclyl or heteroaryl; —OR$_5$, —CN, —N$_3$, —NR$_5$R$_6$, —C(=O)

$NR_5R_6$, $-NR_5C(=O)R_6$, $-C(=O)OR_6$, $-SR_5$, $-SOR_5$ and $-SO_2R_5$; $NR_5C(=O)OR_6$, $-NR_5C(=O)NR_5R_6$, $-O(C=O)R_5$, $-O(C=O)NR_5$, $-NR_5SO_2R_6$, aryl or heteroaryl; and $R_5$, $R_6$, are each independently hydrogen, alkyl, cycloalkyl, aryl, heterocyclyl or heteroaryl; or a pharmaceutically acceptable salt, prodrug, solvate, stereoisomer, racemate, or tautomer thereof.

In a further embodiment, $R_2$ and $R_3$ are each hydrogen and $R_1$ is selected from the group consisting of methyl, benzyl, 2-methoxy ethyl, and ethyl acetate.

In another embodiment, the composition comprises one or more small molecules that increase the gene expression of Atoh1.

In one embodiment, the composition comprises one or more small molecules that increase the protein expression of Atoh1.

In a certain embodiment, the composition comprises one or more small molecules that increase the activity of Atoh1 protein.

In a further embodiment, the one or more small molecules that increase gene expression of Atoh 1, increase protein expression of Atoh 1, or increase the activity of Atoh 1 protein is selected from the group consisting of: CHIR99021, 1-Azakenpaullone, and (2'Z,3'E)-6-Bromoindirubin-3'-oxime (BIO).

In a particular embodiment, the composition comprises a biodegradable polymer.

In an additional embodiment, the composition is administered to the middle ear of the subject.

In another embodiment, the composition is administered onto or adjacent to the round window membrane.

In one embodiment, the composition is administered to the inner ear of the subject.

In one particular embodiment, the composition is administered to the cochlea of the subject.

In one certain embodiment, the composition is administered to the Organ of Corti of the subject.

In one additional embodiment, the composition is administered by transtympanic administration.

In one further embodiment, the composition is administered by transtympanic wick.

In another embodiment, the composition is administered by transtympanic catheter.

In yet another embodiment, the composition is administered by intracochlear injection.

In various embodiments, the invention contemplates, in part, a method for promoting cochlear hair cell regeneration comprising administering, to a middle or inner ear of a subject, a composition comprising an ellipticine derivative in an amount effective and for a time sufficient to promote cochlear hair cell proliferation, thereby promoting cochlear hair cell regeneration.

In a particular embodiment, the ellipticine derivative is a compound of Structure I:

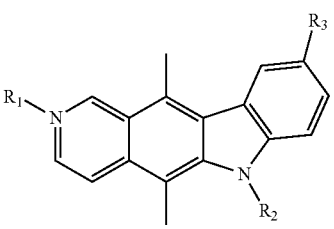

wherein $R_1$ is hydrogen, alkyl, cycloalkyl, cycloalkylalkyl, aryl, aralkyl, heterocyclyl, heterocyclylalkyl, heteroaryl or heteroarylalkyl, wherein $R_1$ is optionally substituted with one or more $R_4$; $R_2$ is, independently, hydrogen, alkyl, haloalkyl, $-CN$, $-C(=O)NR_5R_6$, $-C(=O)OR_5$, $-SO_2R_5$, -aryl or heteroaryl, wherein each $R_2$ is optionally substituted with one or more $R_4$; $R_3$ is, independently, hydrogen, halogen, alkyl, haloalkyl, $-OR_5$, $-CN$, $-N_3$, $-NR_5R_6$, $-C(=O)NR_5R_6$, $-NR_5C(=O)R_6$, $-C(=O)OR_6$, $-SR_5$, $-SOR_5$ and $-SO_2R_5$; $NR_5C(=O)OR_6$, $-NR_5C(=O)NR_5R_6$, $-O(C=O)R_5$, $-NR_5SO_2R_6$, aryl or heteroaryl; each $R_4$, is independently, hydrogen, alkyl, cycloalkyl, aryl, heterocyclyl or heteroaryl; $-OR_5$, $-CN$, $-N_3$, $-NR_5R_6$, $-C(=O)NR_5R_6$, $-NR_5C(=O)R_6$, $-C(=O)OR_6$, $-SR_5$, $-SOR_5$ and $-SO_2R_5$; $NR_5C(=O)OR_6$, $-NR_5C(=O)NR_5R_6$, $-O(C=O)R_5$, $-O(C=O)NR_5$, $-NR_5SO_2R_6$, aryl or heteroaryl; and $R_5$, $R_6$, are each independently hydrogen, alkyl, cycloalkyl, aryl, heterocyclyl or heteroaryl; or a pharmaceutically acceptable salt, prodrug, solvate, stereoisomer, racemate, or tautomer thereof.

In one particular embodiment, $R_2$ and $R_3$ are each hydrogen and $R_1$ is selected from the group consisting of methyl, benzyl, 2-methoxy ethyl, and ethyl acetate.

In a certain particular embodiment, the composition comprises one or more small molecules that increase the gene expression of Atoh 1, increase the protein expression of Atoh 1, or increase the activity of Atoh 1 protein.

In an additional particular embodiment, the one or more small molecules is selected from the group consisting of: CHIR99021, 1-Azakenpaullone, and BIO.

In a further particular embodiment, the composition comprises a biodegradable polymer.

In another particular embodiment, administration of the composition comprises contacting one or more support cells with the composition.

In another embodiment, the contacted one or more support cells proliferate.

In a further embodiment, the contacted one or more support cells dedifferentiate.

In an additional embodiment, the contacted one or more support cells differentiate to a sensory hair cell.

In a certain embodiment, the contacted one or more support cells transdifferentiates to a sensory hair cell.

In a particular embodiment, the support cell is selected from the group consisting of: border cells, inner pillar cells, outer pillar cells, inner phalangeal cells, Dieter's cells and Hensen's cells.

In one embodiment, the composition is locally administered to a middle ear of a subject.

In another embodiment, the composition is locally administered to a inner ear of a subject.

In a particular embodiment, the composition is formulated as an injectable depot.

In a certain embodiment, the local administration comprises transtympanic administration. In a further embodiment, the local administration comprises a trans-tympanic wick. In an additional embodiment, the local administration comprises a trans-tympanic catheter.

In various embodiments, the invention contemplates, in part, a method for treating hearing loss in a subject comprising administering to a middle or inner ear of the subject, a composition comprising an ellipticine derivative in an amount effective and for a time sufficient to improve hearing in the subject.

In a certain embodiment, the improvement in hearing is measured by pure tone audiometry, a speech discrimination test, or a tympanometry test.

In an additional embodiment, the subject has a partial or complete loss of hearing.

In a particular embodiment, the subject has sensorineural hearing loss due to acute or chronic exposure to ototoxic compounds, acute or chronic exposure to noise, age related hearing loss, a genetic related hearing loss, or has auditory neuropathy.

In a certain embodiment, the subject is at risk of developing sensorineural hearing loss or auditory neuropathy.

In an additional embodiment, the ellipticine derivative is a compound of Structure I:

wherein $R_1$ is hydrogen, alkyl, cycloalkyl, cycloalkylalkyl, aryl, aralkyl, heterocyclyl, heterocyclylalkyl, heteroaryl or heteroarylalkyl, wherein $R_1$ is optionally substituted with one or more $R_4$; $R_2$ is, independently, hydrogen, alkyl, haloalkyl, —CN, —C(=O)NR$_5$R$_6$, —C(=O)OR$_5$, —SO$_2$R$_5$, -aryl or heteroaryl, wherein each $R_2$ is optionally substituted with one or more $R_4$; $R_3$ is, independently, hydrogen, halogen, alkyl, haloalkyl, —OR$_5$, —CN, —N$_3$, —NR$_5$R$_6$, —C(=O)NR$_5$R$_6$, —NR$_5$C(=O)R$_6$, —C(=O)OR$_6$, —SR$_5$, —SOR$_5$ and —SO$_2$R$_5$; NR$_5$C(=O)OR$_6$, —NR$_5$C(=O)NR$_5$R$_6$, —O(C=O)R$_5$, —NR$_5$SO$_2$R$_6$, aryl or heteroaryl; each $R_4$, is independently, hydrogen, alkyl, cycloalkyl, aryl, heterocyclyl or heteroaryl; —OR$_5$, —CN, —N$_3$, —NR$_5$R$_6$, —C(=O)NR$_5$R$_6$, —NR$_5$C(=O)R$_6$, —C(=O)OR$_6$, —SR$_5$, —SOR$_5$ and —SO$_2$R$_5$; NR$_5$C(=O)OR$_6$, —NR$_5$C(=O)NR$_5$R$_6$, —O(C=O)R$_5$, —O(C=O)NR$_5$, —NR$_5$SO$_2$R$_6$, aryl or heteroaryl; and $R_5$, $R_6$, are each independently hydrogen, alkyl, cycloalkyl, aryl, heterocyclyl or heteroaryl; or a pharmaceutically acceptable salt, prodrug, solvate, stereoisomer, racemate, or tautomer thereof.

In a further embodiment, $R_2$ and $R_3$ are each hydrogen and $R_1$ is selected from the group consisting of: methyl, benzyl, 2-methoxy ethyl, and ethyl acetate.

In one embodiment, the composition comprises one or more small molecules that increase the gene expression of Atoh 1, increase the protein expression of Atoh 1, or increase the activity of Atoh 1 protein.

In a particular embodiment, the one or more small molecules is selected from the group consisting of: CHIR99021, 1-Azakenpaullone, and BIO.

In an additional embodiment, the composition comprises a biodegradable polymer.

In a certain embodiment, the composition is administered to the middle ear of the subject.

In a further embodiment, the composition is administered onto or adjacent to the round window membrane.

In one embodiment, the composition is administered to the inner ear of the subject.

In another embodiment, the composition is administered to the cochlea of the subject.

In a certain embodiment, the composition is administered to the Organ of Corti of the subject.

In a particular embodiment, the composition is administered by transtympanic administration.

In a certain particular embodiment, the composition is administered by transtympanic wick.

In a further embodiment, the composition is administered by transtympanic catheter.

In one embodiment, the composition is administered by intracochlear injection.

In various embodiments, the invention contemplates, in part, a method for treating a subject who has hearing loss or is at risk of developing hearing loss comprising: identifying a subject having hearing loss or at risk of developing hearing loss; administering to a middle ear or an inner ear of the subject an ellipticine derivative in an amount effective to promote cochlear hair cell regeneration; thereby treating the subject.

In one embodiment, the subject is identified as having hearing loss or at risk of developing hearing loss by pure tone audiometry, a speech discrimination test, or a tympanometry test.

In another embodiment, the subject has a partial or complete loss of hearing.

In yet another embodiment, the subject has sensorineural hearing loss due to acute or chronic exposure to ototoxic compounds, acute or chronic exposure to noise, age related hearing loss, a genetic related hearing loss, or has auditory neuropathy.

In a particular embodiment, the ellipticine derivative is a compound of Structure I:

wherein $R_1$ is hydrogen, alkyl, cycloalkyl, cycloalkylalkyl, aryl, aralkyl, heterocyclyl, heterocyclylalkyl, heteroaryl or heteroarylalkyl, wherein $R_1$ is optionally substituted with one or more $R_4$; $R_2$ is, independently, hydrogen, alkyl, haloalkyl, —CN, —C(=O)NR$_5$R$_6$, —C(=O)OR$_5$, —SO$_2$R$_5$, -aryl or heteroaryl, wherein each $R_2$ is optionally substituted with one or more $R_4$; $R_3$ is, independently, hydrogen, halogen, alkyl, haloalkyl, —OR$_5$, —CN, —N$_3$, —NR$_5$R$_6$, —C(=O)NR$_5$R$_6$, —NR$_5$C(=O)R$_6$, —C(=O)OR$_6$, —SR$_5$, —SOR$_5$ and —SO$_2$R$_5$; NR$_5$C(=O)OR$_6$, —NR$_5$C(=O)NR$_5$R$_6$, —O(C=O)R$_5$, —NR$_5$SO$_2$R$_6$, aryl or heteroaryl; each $R_4$, is independently, hydrogen, alkyl, cycloalkyl, aryl, heterocyclyl or heteroaryl; —OR$_5$, —CN, —N$_3$, —NR$_5$R$_6$, —C(=O)NR$_5$R$_6$, —NR$_5$C(=O)R$_6$, —C(=O)OR$_6$, —SR$_5$, —SOR$_5$ and —SO$_2$R$_5$; NR$_5$C(=O)OR$_6$, —NR$_5$C(=O)NR$_5$R$_6$, —O(C=O)R$_5$, —O(C=O)NR$_5$, —NR$_5$SO$_2$R$_6$, aryl or heteroaryl; and $R_5$, $R_6$, are each independently hydrogen, alkyl, cycloalkyl, aryl, heterocyclyl or heteroaryl; or a pharmaceutically acceptable salt, prodrug, solvate, stereoisomer, racemate, or tautomer thereof.

In a certain embodiment, the ellipticine derivative, wherein $R_2$ and $R_3$ are each hydrogen and $R_1$ is selected from the group consisting of methyl, benzyl, 2-methoxy ethyl, and ethyl acetate.

In a further embodiment, the composition comprises one or more small molecules that increase the gene expression of Atoh 1, increase the protein expression of Atoh 1, or increase the activity of Atoh 1 protein.

In an additional embodiment, the wherein the one or more small molecules is selected from the group consisting of: CHIR99021, 1-Azakenpaullone, and BIO.

In one embodiment, the composition comprises a biodegradable polymer.

In a certain embodiment, the composition is administered to the middle ear of the subject.

In a further embodiment, the composition is administered onto or adjacent to the round window membrane.

In an additional embodiment, the composition is administered to the inner ear of the subject.

In another embodiment, the composition is administered to the cochlea of the subject.

In a certain embodiment, the composition is administered to the Organ of Corti of the subject.

In a particular embodiment, the composition is administered by transtympanic administration.

In one embodiment, the composition is administered by transtympanic wick.

In another embodiment, the composition is administered by transtympanic catheter.

In another particular embodiment, the composition is administered by intracochlear injection.

DETAILED DESCRIPTION

A. Overview

Figure 1:
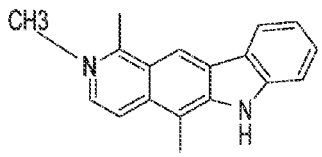
FIG. 1 shows the structure of representative ellipticine derivatives.
Figure 1:
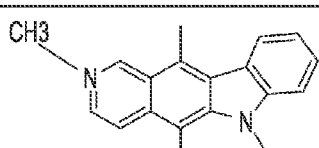
Figure 1:
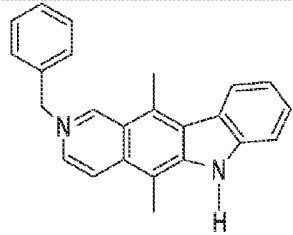
Figure 1:
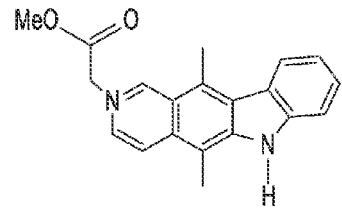
Figure 1:
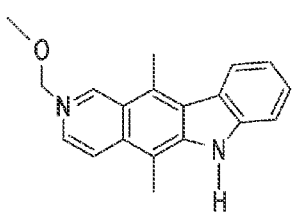

The invention contemplates, in part, compositions and methods for increasing or promoting sensory hair cell regeneration. By increasing or promoting hair cell regeneration, the compositions and methods of the invention are effective in increasing, promoting, or partially or completely restoring sensory hair cell function in a subject that has partial or complete hearing loss and/or balance impairments, whether due to acute or chronic exposure to loud sounds, exposure to ototoxic drugs, disease, genetic disorders, or age-related processes. In humans and other mammals, inner ear hair cell damage results in permanent hearing impairments and/or balance disorders.

Most of the research in sensory hair cell regeneration has been done in avians. In the mature avian cochlea, sensory hair cell damage induces non-sensory supporting cells to undergo either (i) direct transdifferentiation, where a supporting cell changes its gene expression to become a hair cell without dividing, or (ii) mitotic proliferation, where a supporting cell divides to produce two progenitor cells, in order to generate replacement hair cells. While direct transdifferentiation appears to be a rapid and early source of new hair cells (Roberson et al., 2004; Duncan et al., 2006), its overall effectiveness is limited because there is a loss of one supporting cell for each new hair cell made. Thus, there must be a point where supporting cell mitotic proliferation is activated not only to make new hair cells, but also to replace the supporting cells lost to direct transdifferentiation. Ultimately, the regenerating sensory epithelium must produce enough new hair cells and supporting cells to structurally and functionally repopulate the damaged region.

Common genetic pathways between the developing mouse cochlea and the developing and regenerating chick cochlea have been identified (Lewis, 1991; Lee & Cotanche, 1995, 1996; Adam et al, 1998; Fekete & Wu, 2002; Daudet & Lewis, 2005, Stone & Rubel, 1999). However, one major difference identified between mammals and avians was the expression of proliferation inhibitors during organ of Corti development (Chen & Segil, 1999; Lowenheim et al., 1999; Chen et al., 2003; Mantela et al., 2005; Sage et al., 2005, 2006), which is thought to be responsible, in part, for the mature mammalian cochlea's inability to regenerate (Brigande and Heller, 2009).

One such inhibitor, p27 is expressed in cochlear supporting cells from neonates and adult mammals (Chen & Segil, 1999; Minoda et al., 2007). Genetic manipulation of the mammalian cochlea has shown that when p27 expression is knocked down during development, the supporting cells can continue to proliferate beyond their normal embryonic time window, which can lead to the production of excess supporting cells and supernumerary hair cells (Chen & Segil, 1999; Lowenheim et al., 1999). When p27 is down-regulated in cochlea from adult mammals (Minoda et al., 2007; Oesterle et al. 2011), cochlear support cell proliferation is also observed. Moreover, Minoda and colleagues showed that Skp2-mediated proteosomal degradation of p27 was not sufficient to promote hair cell regeneration or induce formation of ectopic hair cells (Minoda et al., *Hear Res.* 2007 October; 232(1-2): 44-51).

The present inventors have discovered that a class of cytotoxic compounds that are also p27 inhibitors can effectively promote or increase hair cell regeneration in the cochlea and thus fill a crucial void in the art for small molecule therapies for hearing loss and/or balance impairments.

In various embodiments, the present invention contemplates, in part compositions and methods that promote or increase sensory hair cell regeneration in a subject. Without wishing to be bound to any particular theory, it is contemplated that in particular embodiments, the compositions and methods promote or increase support cell dedifferentiation and subsequent differentiation of the dedifferentiated cells to regenerate sensory hair cells. In certain embodiments, the compositions and methods of the invention promote or increase transdifferentiation of support cells to sensory hair cells. In additional embodiments, the compositions and methods of the invention promote or increase sensory hair cell regeneration by both the dedifferentiation/differentiation and transdifferentiation pathways. The inventive compositions and methods disclosed herein are also useful for promoting, increasing, and/or partially or completely restoring auditory and/or vestibular function in a subject.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, DNA Cloning: *A Practical Approach*, vol. I & II (IRL Press, Oxford, 1985); Anand, T*echniques for the Analysis of Complex Genomes*, (Academic Press, New York, 1992); T*ranscription and Translation* (B. Hames & S. Higgins, Eds., 1984); Perbal, *A Practical Guide to Molecular Cloning* (1984); and Harlow and Lane, *Antibodies*, (Cold Spring Harbor Laboratory Press, Cold Spring Harbor, N.Y., 1998).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

As used herein, the term "substantially" refers to a quantity, level, concentration, value, number, frequency, percentage, dimension, size, amount, weight or length that is 95%, 96%, 97%, 98%, 99% or 100% of a reference value. For example, a composition that is substantially free of a substance, e.g., a detergent, is 95%, 96%, 97%, 98%, 99% or 100% free of the specified substance, or the substance is undetectable as measured by conventional means. Similar meaning can be applied to the term "absence of," where referring to the absence of a particular substance or component of a composition.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The present invention contemplates, in part, compounds that promote or increase sensory hair cell regeneration.

"Amino" refers to the —$NH_2$ radical.

"Cyano" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_b R_d$ where $R_d$ is an alkylene chain as defined above and $R_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_b R_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_b R_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles.

For example, "substituted" includes any of the above groups in which one or more hydrogen atoms are replaced with —$NR_gR_h$, —$NR_gC(=O)R_h$, —$NR_gC(=O)NR_gR_{11}$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomeric forms of the compounds disclosed herein.

A "derivative" refers to a compound comprising one or more substitutions compared to the reference compound. For example, in one embodiment, ellipticine derivatives are formed by substitution at atom positions 2, 6, and/or 9 of the ellipticine structure. In particular embodiments, ellipticine derivatives are substituted with the chemical groups described herein. However, one would recognize that addition chemical groups can be substituted by suitable methods known to the skilled chemist, so long as the ellipticine derivatives retain a desired biological activity, e.g., increasing sensory hair cell regeneration and/or support cell dedifferentiation and/or proliferation.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

The present invention relates generally to methods for regenerating cells in the inner ear, thus, a brief review of the anatomy of the ear may be helpful in understanding the invention.

The anatomy of the ear is well known to those of ordinary skill in the art (see, e.g., Gray's Anatomy, Revised American Edition (1977), pages 859-867, incorporated herein by reference). The ear is generally divided into three portions: the outer ear, middle ear, and inner ear. The outer ear is composed of the pinna, the auditory canal, and the outward facing portion of the tympanic membrane (ear drum). The function of the outer ear, in part, is to collect and direct sound waves through the auditory canal towards the tympanic membrane and the middle ear.

The middle ear is an air-filled cavity that includes the tympanic cavity, three ear bones (auditory ossicles): the malleus, the incus and the stapes, and oval window, which connects the middle ear with the inner ear. The auditory ossicles are arranged to provide a mechanical linkage between the tympanic membrane and the oval window to the fluid-filled inner ear, where sound is transformed and transduced to the inner ear for further processing.

The inner ear includes three sensory portions: the cochlea, which senses sound; the semicircular canals, which sense angular acceleration; and the otolithic organs (utricle and saccule), which sense linear acceleration; and the round window that connects the cochlea to the middle ear. In each of these sensory portions, specialized sensory hair cells are arrayed upon one or more layers of inner ear supporting cells. Supporting cells underlie, at least partially surround, and physically support sensory hair cells within the inner ear. In operation, the sensory hair cells are physically deflected in response to sound or motion, and their deflection is transmitted to nerves which send nerve impulses to the brain for processing and interpretation.

In particular, the cochlea includes the Organ of Corti which is primarily responsible for sensing sound. The Organ of Corti includes a basilar membrane upon which are located a variety of supporting cells, including border cells, inner pillar cells, outer pillar cells, inner phalangeal cells, Dieter's cells and Hensen's cells. Supporting cells support inner hair cells and outer hair cells. The tectorial membrane is disposed above inner hair cells and outer hair cells. In certain embodiments, the present invention is directed, in part, to stimulating regeneration of sensory hair cells through dedifferentiation and/or proliferation of underlying support cells. In another embodiment, the present invention contemplates the regeneration of sensory hair cells through transdifferentiation of the supporting cells to sensory hair cells.

"Support cells" refers to border cells, inner pillar cells, outer pillar cells, inner phalangeal cells, Dieter's cells and Hensen's cells. In various embodiments, dedifferentiation and proliferation of support cells is achieved, in part, by exposing the support cells to compositions of the invention. In further embodiments, the compositions of the invention also promote the differentiation of the dedifferentiated and/or proliferated support cells to sensory hair cells. In various other embodiments, support cells exposed to compositions of the invention are transdifferentiated to sensory hair cells.

As used herein, the terms "transdifferentiation" or "differentiation plasticity" refers to the conversion of one differentiated cell type into another differentiated cell type. In particular embodiments, transdifferentiation does not include dedifferentiation of the first differentiated cell type and subsequent differentiation of the dedifferentiated cell into the second differentiated cell type. Thus, in particular embodiments, transdifferentiation refers to the direct conversion of one differentiated cell type into another differentiated cell type. For example, a hematopoietic stem cell cultured in such a way as to differentiate into a cell of the neural lineage is said to transdifferentiate.

As used herein, the term "differentiation" refers to a developmental process whereby cells become specialized for a particular function, for example, where cells acquire one or more morphological characteristics and/or functions different from that of the initial cell type. Differentiation decreases the developmental potency of the cell compared to the cell state before differentiation. The term "differentiation" includes both lineage commitment and terminal differentiation processes. States of undifferentiation or differentiation may be assessed, for example, by assessing or monitoring the presence or absence of biomarkers using immunohistochemistry or other procedures known to a person skilled in the art.

As used herein, the term "dedifferentiation" or "reprogramming" refers to a cell that becomes less specialized or more "plastic." Dedifferentiation of cells increase the developmental potency of the cell compared to the cell state prior to dedifferentiation.

As used herein, the term "potency" means the sum of all developmental options accessible to the cell (i.e., the developmental potency). By way of a non-limiting example, a cell in a terminally differentiated state, such as B-lymphocyte, has relatively little developmental potency in that state. On the other hand, zygotes are cells that are in an undifferentiated state and have the highest degree of potency. One having ordinary skill in the art is familiar with the concepts of various levels of potency, including, but not limited to, totipotency, pluripotency, multipotency, and unipotency. It would also be clear to one having skill in the art that potency can be partially or completely altered to any point along the developmental lineage of a cell (i.e., from totipotent to terminally differentiated cell), regardless of cell lineage.

As used herein, the terms "inducing," "promoting," "enhancing," "stimulating," or "increasing" generally refer to the ability of a composition of the invention to produce or cause a greater physiological response (i.e., measurable downstream effect), as compared to the response caused by either vehicle or a control molecule/composition. Such measurable physiological response include, without limitation, an increase in support cell number and/or proliferation, an increase in sensory hair cell number, a decrease in p27 protein levels and/or activity, an increase in Atoh 1 gene/protein expression or Atoh 1 protein activity, and/or increase in the markers of cell proliferation, e.g., an increase in phosphorylated histone H3. The measurable physiological response is compared to normal, untreated, or control-treated cells or tissues. For example, the physiological response may be increased by at least 5%, 10%, 20%, 30%, 40%, 50%, 60%, 70%, 80%, 90%, 100%, 125%, 150%, 175%, 200%, or greater. In another non-limiting example, sensory hair cell regeneration, e.g., the number of new sensory hair cells, in response to administration of a composition of the invention may be increased by at least 5%, 10%, 20%, 30%, 40%, 50%, 60%, 70%, 80%, 90%, 100%, 125%, 150%, 175%, 200%, or greater, compared to normal, untreated, or control-treated cochlear or vestibular cells or tissues. In another non-limiting example, the physiological response in a subject that is increased in response to administration of a composition of the invention is an increase in auditory (hearing) or vestibular function (balance) in the subject of at least 5%, 10%, 20%, 30%, 40%, 50%, 60%, 70%, 80%, 90%, 100%, 125%, 150%, 175%, 200%, or greater, compared to the auditory or vestibular function in the subject before administration of the composition. An "increased," "promoted" or "enhanced" response is typically a "statistically significant" response, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

As used herein, the terms "retaining" or "maintaining," or "retain" or "maintain", generally refer to the ability of a composition of the invention to produce or cause a physiological response (i.e., measurable downstream effect) that prevents the further loss or decrease in auditory or vestibular function in the subject. For example, compositions of the invention that maintain the auditory and/or vestibular function in a subject allow the subject to retain at least at least 75%, at least 80%, at least 85%, at least 90%, at least 95% or about 100% of the level of auditory and/or vestibular function present in the subject prior to the subject being administered a composition of the invention.

As used herein, the terms "decrease" or "lower," or "lessen," or "reduce," or "abate" refers generally to the ability of a composition of the invention to produce or cause a lesser physiological response (i.e., downstream effects), as compared to the response caused by either vehicle or a control molecule/composition, e.g., decreased apoptosis. In one embodiment, the decrease can be a decrease in gene expression or a decrease in cell signaling that normally is associated with a reduction of cell viability. A "decrease" or "reduced" response is typically a "statistically significant" response, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

C. Ellipticine Derivatives

The present inventors have discovered that certain cytotoxic compounds, e.g., ellipticine derivatives, which are used in the treatment of cancer, are also unexpectedly useful in sensory hair cell regeneration. In particular, the invention contemplates that ellipticine derivatives increase or promote the regeneration of hair cells. As a class, ellipticine and derivatives thereof are routinely used as anti-neoplastic compounds. Without wishing to be bound to any particular theory, the present invention contemplates, in part, that the ellipticine derivatives disclosed herein can increase or promote sensory hair cell regeneration by various mechanisms. For example, in some embodiments, an ellipticine derivative promotes or increases support cell dedifferentiation and/or proliferation and then may subsequently promote or increase differentiation of the dedifferentiated and/or proliferated cells to sensory hair cells, e.g., cochlear or vestibular sensory hair cells. In another non-limiting example, an ellipticine derivative may promote or increase the transdifferentiation of the inner ear support cells to sensory hair cells.

In particular embodiments, ellipticine derivatives are used in combination with one or more agents, e.g., small molecules, to synergistically increase or promote sensory hair cell regeneration by any of the various mechanisms described herein or otherwise recognized in the art.

Ellipticine derivatives of the invention are useful for increasing, promoting, or partially or completely restoring sensory hair cell function in an subject that has partial or complete hearing loss and/or balance impairments, whether due to acute or chronic exposure to loud sounds, exposure to ototoxic drugs, disease, genetic disorders, or age-related processes. In certain embodiments, ellipticine derivatives used in the methods of the invention can be any ellipticine derivative that has an activity that promotes or increases support cell proliferation and/or dedifferentiation and/or sensory hair cell regeneration by any of the various mechanisms described herein or otherwise recognized in the art. In particular embodiments, the ellipticine derivatives used in the compositions and methods of the invention are commercially available ellipticine derivatives or derivatives that have an activity that promotes or increases support cell proliferation and/or dedifferentiation and/or sensory hair cell regeneration by any of the various mechanisms described herein or otherwise recognized in the art.

In preferred embodiments, the ellipticine derivatives used in the compositions and methods of the present invention include ellipticine derivatives having structure (I) or a pharmaceutically acceptable salt, prodrug, solvate, stereoisomer, racemate, or tautomer thereof. In one preferred embodiment, ellipticine derivatives of structure (I) include:

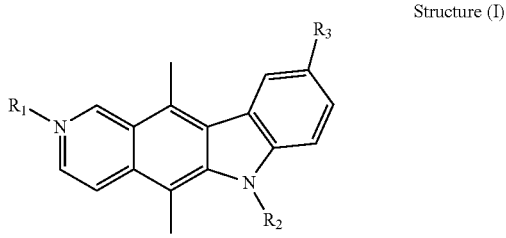

Structure (I)

wherein $R_1$ is hydrogen, alkyl, cycloalkyl, cycloalkylalkyl, aryl, aralkyl, heterocyclyl, heterocyclylalkyl, heteroaryl or heteroarylalkyl, wherein $R_1$ is optionally substituted with one or more $R_4$;

$R_2$ is, independently, hydrogen, alkyl, haloalkyl, —CN, —C(=O)NR$_5$R$_6$, —C(=O)OR$_5$, —SO$_2$R$_5$, -aryl or heteroaryl, wherein each $R_2$ is optionally substituted with one or more $R_4$;

$R_3$ is, independently, hydrogen, halogen, alkyl, haloalkyl, —OR$_5$, —CN, —N$_3$, —NR$_5$R$_6$, —C(=O)NR$_5$R$_6$, —NR$_5$C(=O)R$_6$, —C(=O)OR$_6$, —SR$_5$, —SOR$_5$ and —SO$_2$R$_5$; NR$_5$C(=O)OR$_6$, —NR$_5$C(=O)NR$_5$R$_6$, —O(C=O)R$_5$, —NR$_5$SO$_2$R$_6$, aryl or heteroaryl;

each $R_4$, is independently, hydrogen, alkyl, cycloalkyl, aryl, heterocyclyl or heteroaryl; —OR$_5$, —CN, —N$_3$, —NR$_5$R$_6$, —C(=O)NR$_5$R$_6$, —NR$_5$C(=O)R$_6$, —C(=O)OR$_6$, —SR$_5$, —SOR$_5$ and —SO$_2$R$_5$; NR$_5$C(=O)OR$_6$, —NR$_5$C(=O)NR$_5$R$_6$, —O(C=O)R$_5$, —O(C=O)NR$_5$, —NR$_5$SO$_2$R$_6$, aryl or heteroaryl; and $R_5$, $R_6$, are each independently hydrogen, alkyl, cycloalkyl, aryl, heterocyclyl or heteroaryl; or a pharmaceutically acceptable salt, prodrug, solvate, stereoisomer, racemate, or tautomer thereof.

In another preferred embodiment, the ellipticine derivatives have a structure (I) wherein $R_2$ and $R_3$ are each hydrogen and $R_1$ is selected from the group consisting of methyl, benzyl, 2-methoxyethyl, and ethyl acetate; or a pharmaceutically acceptable salt, prodrug, solvate, stereoisomer, racemate, or tautomer thereof.

It is understood that any embodiment of the compounds of structure (I), as set forth above, and any specific substituent set forth herein for a $R_1$, $R_2$, $R_3$, $R_4$, $R_5$, or $R_6$, group in the compounds of structure (I), as set forth above, may be independently combined with other embodiments and/or substituents of compounds of structure (I) to form additional embodiments of the inventions not specifically set forth above. In addition, in the event that a list of substituents or variables is listed for any particular group in a particular embodiment and/or claim, it is understood that each individual substituent or variable may be deleted from the particular embodiment and/or claim and that the remaining list of substituents and variables will be considered to be within the scope of the invention.

In particular embodiments, the ellipticine derivative is a "prodrug." As used herein, the term "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., A.C.S. Symposium Series, Vol. 14, and in *Bioreversible Carriers in Drug Design*, Ed. Edward B. Roche, American Pharmaceutical Association and Pergamon Press, 1987. In certain embodiments, the term "prodrug" also refers to any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

In particular embodiments, ellipticine derivatives include all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Examples as set out below using an appropriate isotopically-labeled reagent in place of the non-labeled reagent previously employed.

In certain embodiments, the ellipticine derivatives disclosed herein also encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

In particular embodiments, the ellipticine derivatives of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

For the purposes of administration, the compounds of the present invention may be administered as a raw chemical or may be formulated as pharmaceutical compositions as described elsewhere herein.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

D. Small Molecule Inducers of Atoh 1 (Math 1) Expression and/or Activity

The invention contemplates, in part, compositions and methods for promoting or increasing sensory hair cell regeneration in the cochlea and vestibular organs, wherein the compositions comprise at least one ellipticine derivative and one or more small molecules that induce or increase Atoh 1 expression or activity. Atoh 1 is an E-box transcription factor that is normally expressed during cochlear and vestibular hair cell development. In certain instances, mice with Atoh 1 knocked-out did not develop hair cells. However, in certain instances, adenoviruses expressing Atoh 1 stimulates the growth and/or regeneration of hair cells in guinea pigs treated with ototoxic antibiotics. Accordingly, particular embodiments of the invention include compositions comprising one or more ellipticine derivatives and a small molecule inducer that induces or increases expression of the Atoh 1 gene or protein and/or activity of Atoh 1 protein.

Without wishing to be bound to any particular theory, it is contemplated that inducing or increasing Atoh1 expression or activity in dedifferentiated and/or proliferating support cells may increase the regeneration of sensory hair cells in the cochlea and vestibular organs compared to compositions lacking a small molecule inducer of Atoh 1 expression or activity.

As used herein, the terms "small molecule," "compound," "substance," and "agent" are used interchangeably herein, to refer to natural or synthetic small organic or inorganic compounds having a molecular weight of more than 50 and less than about 2,500 Daltons.

In one embodiment, the small molecule is a GSK-3 inhibitor that induces Atoh 1 expression.

Small molecule inducers of Atoh 1 expression, e.g., gene expression or protein expression, may induce or increase Atoh 1 mRNA or protein expression about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, or more percent compared to an cell that has not been exposed to the small molecule.

Small molecule inducers of Atoh 1 activity, e.g., activity of Atoh 1 protein, may induce or increase Atoh 1 activity about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 200%, about 300%, about 400%, about 500%, or more percent compared to an cell that has not been exposed to the small molecule.

The term "small molecule" encompasses numerous biological and chemical classes, including synthetic, semi-synthetic, or naturally-occurring inorganic or organic molecules, including synthetic, recombinant or naturally-occurring compounds. In particular embodiments, small molecules are obtained from a combinatorial small organic molecule or peptide library containing a large number of potential therapeutic compounds. Such "combinatorial chemical libraries" or "ligand libraries" can be screened separately or screened in pools, to identify those library members particular chemical species or subclasses that display the desired characteristic activity of inducing or increasing Atoh 1 mRNA or protein expression or increasing the activity of Atoh 1 protein. In certain embodiments, screening libraries with pools of compounds may reduce the ultimate number of screens for any given library. For example, pools containing the activity of interest can be iteratively subdivided until the activity is restricted to a particular compound or mixture of compounds. The identified compounds can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks in every possible way for a given compound length. Millions of chemical compounds can be synthesized through such combinatorial mixing of chemical building blocks. Preparation and screening of combinatorial chemical libraries is well known to those of skill in the art. Such combinatorial chemical libraries include, but are not limited to, peptide libraries (see, e.g., U.S. Pat. No. 5,010,175; Furka, *Int. J. Pept. Prot. Res.* 1991; 37:487-493 and Houghton et al., *Nature.* 1991; 354:84-88). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA.* 1993; 90:6909-6913), vinylogous polypeptides (Hagihara et al., *J. Amer. Chem. Soc.* 1992; 114:6568), nonpeptidal peptidomimetics with glucose scaffolding (Hirschmann et al., *J. Amer. Chem. Soc.* 1992; 114:9217-9218), analogous organic syntheses of small compound libraries (Chen et al., *J. Amer. Chem. Soc.* 1994; 116:2661), oligocarbamates (Cho et al., *Science.* 1993; 261:1303), and/or peptidyl phosphonates (Campbell et al., *J. Org. Chem.* 1994; 59:658), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., *Science.* 1996; 274: 1520-1522 and U.S. Pat. No. 5,593,853), small organic molecule libraries (see, e.g., benzodiazepines, Baum, *C&EN.* 1993; Jan. 18, page 33; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514. Additional illustrative examples for the synthesis of molecular libraries can be found in: (Carell et al., 1994a; Carell et al., 1994b; Cho et al., 1993; DeWitt et al., 1993; Gallop et al., 1994; Zuckermann et al., 1994). In addition, libraries of natural compounds in the form of bacterial, fungal, plant and animal extracts are available from Pan Labs (Bothell, Wash.) or are readily producible.

Small molecules may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents, particularly candidate agents, are also found among biomolecules including peptides, saccharides, fatty acids, steroids, purines, pyrimidines, derivatives, structural analogs or combinations thereof.

In other embodiments, the small molecule can be purified or can be contained in a complex substance. A complex substance is comprised of a plurality of components and/or compounds, including one or more small molecules. A complex substance can, for example, be an animal's body fluid. Suitable animal body fluids include, for example, blood, plasma, serum, bone marrow, urine, cerebrospinal fluid, saliva, synovial fluid, ocular fluid, amniotic fluid, bile, seminal fluid, or secretions. Suitable secretions include pancreatic secretions, gastric secretions, nasal secretions, pulmonary secretions, vaginal secretions, and perspiration. Accordingly, the substances identified herein are in no way limiting. The animal providing the small molecule can be a human subject. Furthermore, there is no need in the context of the invention to identify the nature or any characteristics of the small molecule.

Exemplary small molecules that induce or increase Atoh 1 gene and/or protein expression and/or activity of Atoh 1 protein and that are suitable for use in the compositions and methods of the present invention include, but are not limited to, CHIR99021 (IUPAC name: 6-((2-(4-(2,4-dichlorophenyl)-5-(4-methyl-1H-imidazol-2-yl)pyrimidin-2-yl)amino)ethyl)amino)nicotinonitrile); 1-Azakenpaullone (IUPAC name: 9-bromo-7,12 dihydropyrido[3',':2,3]azepino[4,5-b]indol-6(5H)-one); and BIO (IUPAC name: 6-bromo-3-[(3E)-1,3-dihydro-3-(hydroxyimino)-2H-indol-2-ylidene]-1,3-dihydro-(3Z)-2H-indol-2-one).

E. Compositions and Formulations

Compositions (i.e., medicaments) of the present invention comprise one or more ellipticine derivatives, as described elsewhere or a prodrug, solvate, stereoisomer, racemate, or tautomer thereof, formulated with a pharmaceutically-acceptable salt, carrier, diluent, and/or excipient for administration to a cell or an animal, either alone, or in combination with one or more other modalities of therapy. In particular embodiments, a composition comprises at least one ellipticine derivative of structure (I) or a prodrug, solvate, stereoisomer, racemate, or tautomer thereof, formulated with a pharmaceutically-acceptable carrier, diluent and/or excipient. In other particular embodiments, a composition comprises at least 1, at least 2, at least 3, at least 4, at least 5, or more ellipticine derivatives of structure (I) or a prodrug, solvate, stereoisomer, racemate, or tautomer thereof, formulated with a pharmaceutically-acceptable salt carrier, diluent and/or excipient. In certain embodiments, compositions comprising ellipticine derivatives increase or promote sensory hair cell regeneration by i) promoting or increasing support cell proliferation and/or dedifferentiation and/or subsequent differentiation of the dedifferentiated and/or proliferated cells to sensory hair cells, e.g., cochlear or vestibular sensory hair cells, or ii) transdifferentiation of the inner ear support cells to sensory hair cells.

In particular embodiments, compositions of the invention comprise an effective amount of an ellipticine derivative, or salt, prodrugs, solvates, stereoisomers, racemates, or tautomers thereof, and one or more small molecules that induce or increase expression and/or activity of Atoh 1, formulated with a pharmaceutically-acceptable carrier, diluent and/or excipient. In certain embodiments, compositions comprise at least one ellipticine derivative of structure (I) or salt, prodrugs, solvates, stereoisomers, racemates, or tautomers thereof, and at least one small molecule inducer of Atoh 1, formulated with a pharmaceutically-acceptable salt, carrier, diluent and/or excipient. In particular embodiments, compositions comprising ellipticine derivatives, optionally in combination with one or more small molecules, synergistically increase or promote sensory hair cell regeneration by i) promoting or increasing support cell proliferation, and/or dedifferentiation and/or subsequent differentiation of the dedifferentiated and/or proliferated cells to sensory hair cells, e.g., cochlear or vestibular sensory hair cells, or ii) transdifferentiation of the inner ear support cells to sensory hair cells.

Thus, compositions comprising ellipticine derivatives of the invention, and optionally a small molecule that induces or increases expression and/or activity of Atoh 1, are useful for increasing, promoting, or partially or completely restoring sensory hair cell function in an subject that has partial or complete hearing loss and/or balance impairments, whether due to acute or chronic exposure to loud sounds, exposure to ototoxic drugs, disease, genetic disorders, or age-related processes. Without being bound to any particular theory, it is contemplated that compositions comprising both ellipticine derivates and small molecule inducers of Atoh 1 expression or activity will synergistically increase or promote sensory hair cell regeneration compared to a composition comprising either ellipticine derivatives or small molecule inducers of Atoh 1 expression or activity.

In further embodiments, compositions comprise effective amounts of at least one ellipticine derivative and optionally a small molecule that induces or increases expression and/or activity of Atoh 1, which can be used to stimulate the formation of sensory hair cells from support cells.

Compositions (i.e., medicaments) of the present invention include, but are not limited to pharmaceutical compositions. A "pharmaceutical composition" refers to a formulation of a composition of the invention with one or more pharmaceutically acceptable carriers, diluents or excipients generally accepted in the art for the delivery of the biologically active compounds to mammals, e.g., humans. In particular embodiments, pharmaceutical compositions of the present invention may comprise ellipticine derivatives, small molecule inducers of Atoh 1 expression or activity, or any combination thereof, formulated with one or more pharmaceutically-acceptable carriers, diluents, and/or excipients. It will also be understood that, if desired, the compositions of the invention may be administered in combination with other agents as well, such as, e.g., nucleic acids, proteins, small molecules, or pharmaceutically-active agents, so long as the desired therapeutic effect is achieved. There is virtually no limit to other reagents that may also be included in the compositions, provided that the additional reagents do not adversely affect the desired regenerative therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions of the present invention can be formulated in any manner suitable for a desired delivery route, e.g., transtympanic injection, transtympanic wicks and catheters, and injectable depots. Typically, formulations include all physiologically acceptable compositions. Such formulations may include one or more ellipticine derivatives or prodrugs, solvates, stereoisomers, racemates, or tautomers thereof, one or more small molecules that induces or increases expression and/or activity of Atoh 1 or prodrugs, solvates, stereoisomers, racemates, or tautomers thereof, in combination with any physiologically acceptable carriers, diluents, and/or excipients.

The compositions described herein may provide pharmaceutically acceptable formulations with therapeutically effective amounts of one or more ellipticine derivatives or prodrugs, solvates, stereoisomers, racemates, or tautomers thereof, one or more small molecules that induces or increases expression and/or activity of Atoh 1 or prodrugs, solvates, stereoisomers, racemates, or tautomers thereof, formulated with one or more pharmaceutically acceptable carriers (additives), other active agents, and/or diluents.

Pharmaceutical compositions of the invention are formulated so as to allow the active ingredients contained therein to be bioavailable upon administration of the composition to a subject. The pharmaceutical compositions of the invention can be prepared by combining ellipticine derivatives and/or small molecules with an appropriate pharmaceutically acceptable carrier, diluent or excipient, and may be formulated into preparations in solid, semi-solid, liquid, gels, and microspheres, including those formulations adapted for auricular administration, by transtympanic wicks or catheters, or parenteral administration, for example, by intraauricular, transtympanic, or intracochlear injection. However, in certain embodiments the subject compounds may be simply dissolved or suspended in sterile water.

Solid formulations of the compositions described herein, such as dragees, capsules, pills and granules, may optionally be scored or prepared with coatings and shells, such as enteric coatings and other coatings. Solid dosage forms may also be formulated so as to provide slow or controlled release of the ion channel modulating compound. Thus, solid formulations could include any material that could provide a desired release profile of the ion channel modulating compound, including but not limited to hydroxypropylmethyl cellulose in varying proportions, or other polymer matrices, liposomes and/or microspheres.

Coated, gel, or encapsulating formulations of ellipticine derivatives and/or small molecules may also be formulated to deliver pulsatile, sustained, or extended release. For example, one method of pulsatile release could be achieved by layering multiple coatings of ellipticine derivatives and/or small molecules, or by incorporating the ellipticine derivatives and/or small molecules within different regions of the formulation having different release times.

Liquid dosage formulations may include pharmaceutically acceptable emulsions, microemulsions, solutions, suspensions, syrups and elixirs. In addition, the liquid dosage formulations may contain inert diluents commonly used in the art, including but not limited to water or other solvents; solubilizing agents and emulsifiers, such as ethyl alcohol, isopropyl alcohol, ethyl carbonate, ethyl acetate, benzyl alcohol, benzyl benzoate, propylene glycol, 1,3-butylene glycol; oils (in particular, cottonseed, groundnut, corn, germ, olive, castor and sesame oils); glycerol; tetrahydrofuryl alcohol; polyethylene glycols; and fatty acid esters of sorbitan, and mixtures thereof.

Suspensions formulations include, without limitation, ethoxylated isostearyl alcohols; polyoxyethylene sorbitol and sorbitan esters; microcrystalline cellulose; aluminum metahydroxide; bentonite; agar-agar; tragacanth; and mixtures thereof.

Injectable depot formulations can be made by forming microencapsulated matrices of the composition in biodegradable polymers. Examples of biodegradable polymers include, but are not limited to polylactide-polyglycolide, poly(orthoesters) and poly(anhydrides). The ratio of composition to polymer and the nature of the particular polymer employed can affect the rate of release of ellipticine derivatives and/or small molecules from the composition. Depot injectable formulations can also be prepared by entrapping the drug in liposomes or micro emulsions.

Proper fluidity of liquid, suspension and other formulations of the ion channel modulating compounds can be maintained by the use of coating materials such as lecithin; by the maintenance of the required particle size in the case of dispersions; or by the use of surfactants.

Formulations may also include anti-contamination agents for the prevention of microorganism contamination. Anti-contamination agents may include but are not limited to antibacterial and antifungal agents, for example, paraben, chlorobutanol, phenol sorbic acid, antibiotics, and the like.

Formulations may also be sterilized by, for example, by filtration through a bacteria-retaining filter, or by incorporating sterilizing agents in the form of sterile solid formulations which can be dissolved in sterile water, or some other sterile medium immediately before use or formulation.

Formulations may also be endotoxin free. As used herein, the term "endotoxin free" refers to compositions or formulations that contain at most trace amounts (i.e., amounts having no adverse physiological effects to a subject) of endotoxin, and preferably undetectable amounts of endotoxin. By "substantially free of endotoxin" is meant that there is less endotoxin per dose of cells than is allowed by the FDA for a biologic, which is a total endotoxin of 5 EU/kg body weight per day, which for an average 70 kg person is 350 EU per total dose of cells. In one embodiment, the term "endotoxin free" refers to a composition or formulation that is at least 95%, at least 96%, at least 97%, at least 98%, at least 99%, or 100% endotoxin free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipooligosaccharides (LOS) found in the outer membrane of various Gram-negative bacteria, and which represent a central pathogenic feature in the ability of these bacteria to cause disease. Small amounts of endotoxin in humans can produce fever, a lowering of the blood pressure, and activation of inflammation and coagulation, among other adverse physiological effects. Therefore, it is often desirable to remove most or all traces of endotoxin from drug product containers, because even small amounts may cause adverse effects in humans.

Pharmaceutical compositions may further comprise one or more components that enhance the bioavailability of the active ingredients of the composition, e.g., penetration enhancers, stabilizing agents, and one or more components that provide slow or controlled release of the ellipticine derivatives and/or small molecules in the composition, e.g., biocompatible polymers and/or gels.

In particular embodiments, compositions comprising penetration enhancers will facilitate the delivery of the composition across biological barriers that separate the middle and inner ear, e.g., the round window, thereby efficiently delivery a therapeutically effective amount of the composition to the inner ear. Efficient delivery to the cochlea, Organ of Corti, and/or vestibular organs is desired because these tissues host the support cells that promote sensory hair cell regeneration when treated or contacted with compositions of the present invention.

A "penetration enhancer" or "permeability enhancer" includes a polyol such as polyethylene glycol (PEG), glycerol (glycerin), maltitol, sorbitol etc.; diethylene glycol monoethyl ether, azone, benzalkonium chloride (ADBAC), cetylperidium chloride, cetylmethylammonium bromide, dextran sulfate, lauric acid, menthol, methoxysalicylate, oleic acid, phosphatidylcholine, polyoxyethylene, polysorbate 80, sodium glycholate, sodium lauryl sulfate, sodium salicylate, sodium taurocholate, sodium taurodeoxycholate, sulfoxides, sodium deoxycholate, sodium glycodeoxycholate, sodium taurocholate and surfactants such as sodium lauryl sulfate, laureth-9, cetylpyridinium chloride and polyoxyethylene monoalkyl ethers, benzoic acids, such as sodium salicylate and methoxy salicylate, fatty acids, such as lauric acid, oleic acid, undβcanoic acid and methyl oleate, fatty alcohols, such as octanol and nonanol, laurocapram, cyclodextrins, thymol, limonene, urea, chitosan and other natural and synthetic polymers.

Suitable polyols for inclusion in the solutions of the invention include glycerol and sugar alcohols such as sorbitol, mannitol or xylitol, polyethylene glycol and derivatives thereof. In some embodiments the composition further includes a preservative. Accepted preservatives such as benzalkonium chloride and disodium edetate (EDTA) are included in the compositions of the invention in concentrations sufficient for effective antimicrobial action, about 0.0001 to 0.1%, based on the weight of the composition.

In particular embodiments, compositions of the present invention also include stabilizers to increase the therapeutic lifetime of the compositions in vivo. Exemplary stabilizers include fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In further embodiments, the chosen stabilizer changes the hydrophobicity of the formulation (e.g., oleic acid, waxes), or improves the mixing of various components in the formulation (e.g., ethanol), affects the moisture level in the formula (e.g., PVP or polyvinyl pyrrolidone), affects the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In other embodiments, stabilizers are present in sufficient amounts to inhibit the degradation of the ellipticine derivatives and small molecules in the composition. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In particular embodiments, compositions of the invention are formulated as controlled release formulations. In general, controlled release drug formulations impart control over the release of drug with respect to site of release and time of release in vivo. Controlled release includes to immediate release, delayed release, sustained release, extended release, variable release, pulsatile release and bi-modal release. Advantages offered by controlled release include: less frequent dosing; more efficient drug utilization; localized drug delivery by placement of a delivery device or formulation at a treatment site in vivo; and the opportunity to administer and release two or more different drugs, each having a unique release profile, or to release the same drug at different rates or for different durations, by means of a single dosage unit.

Controlled release formulations may be made by formulating the compositions with biocompatible polymers, viscosity agents, gels, paints, foams, xerogels, microparticles, hydrogels, nanocapsules, and thermoreversible gels, or combinations thereof. In preferred embodiments, the polymer or gels are biodegradable. Release properties are often controlled by the particular combination of polymers or gels used to formulate the composition. These methods are well known in the art.

Exemplary polymers suitable for formulating the inventive compositions include, but are not limited to polyamides, polycarbonates, polyalkylenes (polyethylene glycol (PEG)), polymers of acrylic and methacrylic esters, polyvinyl polymers, polyglycolides, polysiloxanes, polyurethanes and copolymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

In particular embodiments, the polymer is a ABA-type or BAB-type triblock copolymers or mixtures thereof, wherein the A-blocks are relatively hydrophobic and comprise biodegradable polyesters or poly(orthoester), and the B-blocks are relatively hydrophilic and comprise polyethylene glycol (PEG). The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof.

Exemplary viscosity agents suitable for use in formulating compositions of the present invention include, but are not limited to, hydroxypropyl methylcellulose, hydroxyethyl cellulose, polyvinylpyrrolidone, carboxymethyl cellulose, polyvinyl alcohol, sodium chondroitin sulfate, sodium hyaluronate, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, or polyvinylpyrrolidone (PVP: povidone).

Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof.

As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. By way of non-limiting example, paints include collodions (e.g., Flexible Collodion, USP), and solutions comprising saccharide siloxane copolymers and a cross-linking agent. The paints contemplated for use herein, are flexible such that they do not interfere with the propagation of pressure waves through the ear. Further, the paints may be applied as a liquid (i.e., solution, suspension, or emulsion), a semisolid (i.e., a gel, foam, paste, or jelly) or an aerosol.

Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic sidechains, cellulose and derivatives thereof, agar and derivatives thereof, such as agar stabilized with polyacrylamide, polyethylene oxides, glycol methacrylates, gelatin, gums such as xanthum, guar, karaya, gellan, arabic, tragacanth and locust bean gum, or combinations thereof. The formulation optionally further comprises a foaming agent, which promotes the formation of the foam, including a surfactant or external propellant. Examples of suitable foaming agents include cetrimide, lecithin, soaps, silicones and the like. Commercially available surfactants such as Tween™ are also suitable.

In particular embodiments, gel formulations that are useful in practicing the methods of the invention include, but are not limited to, glycerin-based gels, glycerin-derived compounds, conjugated, or crosslinked gels, matrices, hydrogels, and polymers, as well as gelatins and their derivatives, alginates, and alginate-based gels, and various native and synthetic hydrogel and hydrogel-derived compounds.

In some embodiments, the compositions described herein have a concentration of each pharmaceutically active ingredient (i.e., ellipticine derivatives, small molecules, pharmaceutically acceptable salts, prodrugs, solvates, stereoisomers, racemates, or tautomers thereof) of between about 0.01% to about 90%, between about 0.01% to about 50%, between about 0.1% to about 70%, between about 0.1% to about 50%, between about 0.1% to about 40%, between about 0.1% to about 30%, between about 0.1% to about 20%, between about 0.1% to about 10%, or between about 0.1% to about 5%, of the each active ingredient, by weight of the composition.

In some embodiments, the compositions described herein have a concentration of each active pharmaceutical agent between about 1% to about 50%, between about 5% to about 50%, between about 10% to about 40%, or between about 10% to about 30%, of the active ingredient, or pharmaceutically acceptable salt, prodrug, solvate, stereoisomer, racemate, or tautomer thereof, by weight of the composition.

In some embodiments, the formulations described herein have a concentration of active pharmaceutical ingredient of between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable salt, prodrug, solvate, stereoisomer, racemate, or tautomer thereof, by volume of the formulation.

In one embodiment, the formulations disclosed herein additionally provide an immediate release of one or more pharmaceutically active ingredients (i.e., ellipticine derivatives, small molecules, pharmaceutically acceptable salts, prodrugs, solvates, stereoisomers, racemates, or tautomers thereof) from the composition, or within 1 minute, or within 5 minutes, or within 10 minutes, or within 15 minutes, or within 30 minutes, or within 60 minutes or within 90 minutes. In other embodiments, a therapeutically effective amount of at least one pharmaceutically active ingredient (i.e., ellipticine derivatives, small molecules, pharmaceutically acceptable salts, prodrugs, solvates, stereoisomers, racemates, or tautomers thereof) is released from the composition immediately, or within 1 minute, or within 5 minutes, or within 10 minutes, or within 15 minutes, or within 30 minutes, or within 60 minutes or within 90 minutes.

In other embodiments, the composition is formulated as an extended release formulation. In certain embodiments, diffusion of at least one pharmaceutically active ingredient (i.e., ellipticine derivatives, small molecules, pharmaceutically acceptable salts, prodrugs, solvates, stereoisomers, racemates, or tautomers thereof) from the formulation occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one pharmaceutically active ingredient (i.e., ellipticine derivatives, small molecules, pharmaceutically acceptable salts, prodrugs, solvates, stereoisomers, racemates, or tautomers thereof) is released from the formulation for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In further embodiments, the formulation provides both an immediate release and an extended release formulation. In particular embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first pharmaceutically active ingredient (i.e., ellipticine derivatives, small molecules, pharmaceutically acceptable salts, prodrugs, solvates, stereoisomers, racemates, or tautomers thereof) and an extended release of a second pharmaceutically active ingredient or other therapeutic agent. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first pharmaceutically active ingredient and second pharmaceutically active ingredient.

The combination of immediate release, delayed release and/or extended release compositions or formulations may be combined with other pharmaceutical agents, as well as the excipients, diluents, stabilizers, carrier agents and other components disclosed herein. As such, depending upon the components of the composition, the thickness or viscosity desired, or the mode of delivery chosen, alternative aspects of the embodiments disclosed herein are combined with the immediate release, delayed release and/or extended release embodiments accordingly.

F. Administration

Compositions of the present invention can be administered by a number of methods sufficient to deliver the composition to the inner ear. Delivering a composition to the inner ear includes administering the composition to the middle ear, such that the composition may diffuse across the round window to the inner ear and administering a composition to the inner ear by direct injection through the round window membrane. Such methods include, but are not limited to auricular administration, by transtympanic wicks or catheters, or parenteral administration, for example, by intraauricular, transtympanic, or intracochlear injection.

In particular embodiments, the compositions and formulations of the invention are locally administered, meaning that they are not administered systemically.

As used herein, the term "auricular administration" refers to a method of using a catheter or wick device to administer a composition across the tympanic membrane to the inner ear of the subject. To facilitate insertion of the wick or catheter, the tympanic membrane may be pierced using a suitably sized syringe. The devices could also be inserted using any other methods known to those of skill in the art, e.g., surgical implantation of the device. In particular embodiments, the wick or catheter device may be a stand alone device, meaning that it is inserted into the ear of the subject and then the composition is controllably released to the inner ear. In other particular embodiments, the wick or catheter device may be attached or coupled to a pump or other device that allows for the administration of additional compositions. The pump may be automatically programmed to deliver dosage units or may be controlled by the subject or medical professional.

As used herein, the term "intraauricular administration" refers to administration of a composition to the middle or inner ear of a subject by directly injecting the composition. "Transtympanic" administration refers to direct injection of a composition across the tympanic membrane into the middle ear. "Intracochlear" administration refers to direct injection of a composition across the tympanic membrane and across the round window membrane into the cochlea. "Intravestibular" administration refers to direct injection of a composition across the tympanic membrane and across the round window membrane into the vestibular organs.

In one embodiment, a syringe and needle apparatus is used to administer compositions to a subject using auricular administration. A suitably sized needle is used to pierce the tympanic membrane and a wick or catheter comprising the composition is inserted through the pierced tympanic membrane and into the middle ear of the subject. The device may be inserted such that it is in contact with the round window or immediately adjacent to the round window. Exemplary devices used for auricular administration include, but are not limited to, transtympanic wicks, transtympanic catheters, round window microcatheters (small catheters that deliver medicine to the round window), and Silverstein Microwicks™ (small tube with a "wick" through the tube to the round window, allowing regulation by subject or medical professional).

In another embodiment, a syringe and needle apparatus is used to administer compositions to a subject using transtympanic injection, injection behind the tympanic membrane into the middle and/or inner ear. The formulation may be administered directly onto the round window membrane via transtympanic injection or may be administered directly to the cochlea via intracochlear injection or directly to the vestibular organs via intravestibular injection.

In some embodiments, the delivery device is an apparatus designed for administration of compositions to the middle and/or inner ear. By way of example only: GYRUS Medical Gmbh offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver compositions to the inner ear. U.S. Patent Application Publication 2007/0167918, which is incorporated herein by reference for such disclosure, further describes a combined otic aspirator and medication dispenser for transtympanic fluid sampling and medicament application.

In some embodiments, a composition disclosed herein is administered to an subject in need thereof once. In some embodiments, a composition disclosed herein is administered to an subject in need thereof more than once. In some embodiments, a first administration of a composition disclosed herein is followed by a second, third, fourth, or fifth administration of a composition disclosed herein.

The number of times a composition is administered to an subject in need thereof depends on the discretion of a medical professional, the disorder, the severity of the disorder, and the subject's response to the formulation. In some embodiments, a composition disclosed herein is administered once to an subject in need thereof with a mild acute condition. In some embodiments, a composition disclosed herein is administered more than once to an subject in need thereof with a moderate or severe acute condition. In the case wherein the subject's condition does not improve, upon the doctor's discretion the composition may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the composition may administered continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once the subject's hearing and/or balance has improved, a maintenance dose can be administered, if necessary. Subsequently, the dosage or the frequency of administration, or both, is optionally reduced, as a function of the symptoms, to a level at which the improved disease, disorder or condition is retained. In certain embodiments, subjects require intermittent treatment on a long-term basis upon any recurrence of symptoms.

Actual methods of preparing formulations and dosage forms are known, or will be apparent, to those skilled in this art; for example, see *Remington: The Science and Practice of Pharmacy*, 21st Edition. Baltimore, Md.: Lippincott Williams & Wilkins, 2006.

G. Methods

The present invention contemplates, in part, methods for administering compositions that promote, induce, and/or increase hair cell regeneration in the inner ear of a subject, and methods for increasing hearing or treating or preventing hearing loss. As used herein, the terms "subject," "subject in need of treatment," and "subject in need thereof," are to be used interchangeably and refer to any mammal, including humans, domestic and farm animals, and zoo, sports, and pet animals, such as dogs, horses, cats, sheep, pigs, goats, cows, rats, mice, etc. that is in need of treatment because he is at risk for loss of, or has loss of, hearing and/or balance due to loss (or risk of loss) of support and/or sensory hair cells in the inner ear, e.g., a subject that is taking ototoxic antibiotics, elderly subjects, subjects that are exposed to loud sounds, subjects that have degenerative hearing disorders. The preferred mammal herein is a human, including adults, children, and the elderly.

In one embodiment, a subject has or is at risk of having sensorineural hearing loss, hearing impairment, or imbalance disorders. In particular embodiments, the methods, compounds, and compositions described herein can be used for treating subjects who have, or who are at risk for developing, an inner ear disorder resulting from a loss of sensory hair cells in the cochlea and/or vestibular organs. Subjects with sensory hair cell loss experience the degeneration of cochlea hair cells and may also experience loss of supporting cells in the Organ of Corti. In some embodiments, the invention can be used to promote or increase sensory hair cell regeneration and to treat any disorder that arises as a consequence of sensory hair cell or support cell loss in the inner ear, such as hearing impairments, deafness, and vestibular disorders, for example, by promoting dedifferentiation and/or proliferation of support cells and subsequent differentiation of the dedifferentiated and/or proliferation cells, or by direct transdifferentiation of support cells to sensory hair cells.

In some embodiments, the methods comprise a step of selecting a subject at risk of hair cell loss and/or a subject with hair cell loss. In particular embodiments, the methods comprise a step of selecting a subject at risk of sensorineural hearing loss and/or a subject with sensorineural hearing loss. Any subject experiencing or at risk for developing hearing loss is a candidate for the treatment methods described herein. A human subject having or at risk for developing a hearing loss can hear less well than the average human being, or less well than a human before experiencing the hearing loss. For example, hearing can be diminished by at least 5, 10, 30, 50% or more. In some embodiments, the subject can have sensorineural hearing loss, which results from damage or malfunction of the sensory part (the cochlea) or the neural part (the auditory nerve) of the ear, or conductive hearing loss, which is caused by blockage or damage in the outer and/or middle ear. In certain embodiments, the subject can have mixed hearing loss caused by a problem in both the conductive pathway (in the outer or middle ear) and in the nerve pathway (the inner ear). An example of a mixed hearing loss is a conductive loss due to a middle-ear infection combined with a sensorineural loss due to damage associated with aging.

In some embodiments, the subject can be deaf or have a hearing loss for any reason, or as a result of any type of event. For example, a subject can be deaf because of a genetic or congenital defect; for example, a human subject can have been deaf since birth, or can be deaf or hard-of-hearing as a result of a gradual loss of hearing due to a genetic or congenital defect. In another example, a human subject can be deaf or hard-of-hearing as a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss.

In some embodiments, a subject can experience chemical-induced ototoxicity, wherein ototoxins include therapeutic drugs including antineoplastic agents, salicylates, quinines, and aminoglycoside antibiotics, contaminants in foods or medicinals, and environmental or industrial pollutants.

In some embodiments, a subject can have a hearing disorder that results from aging. In another embodiment, the subject can have tinnitus (characterized by ringing in the ears).

In one embodiment, a subject suitable for the treatment using the methods of the present invention include a subject having a vestibular dysfunction, including bilateral and unilateral vestibular dysfunction. Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunction can be the result of a genetic or congenital defect; an infection, such as a viral or bacterial infection; or an injury, such as a traumatic or nontraumatic injury. Vestibular dysfunction is most commonly tested by measuring individual symptoms of the disorder (e.g., vertigo, nausea, and fuzzy vision).

Tests are known and available for diagnosing hearing impairments. One of the most commonly employed hearing tests is pure tone audiometry that involves measuring the threshold of hearing for pure tones of normally audible frequencies generally varying from 200 to 8000 Hertz. Comparison of pure tone testing of threshold by air (sounds that reach the inner ear through the ear canal) and bone conduction (sounds transmitted through bones) enables discrimination between sensorineural and conductive hearing loss. Speech discrimination tests that measure a person's ability to identify words can also be used as an indicator of sensorineural hearing loss. The test includes presentation of about 50 selected monosyllabic words at an easily detectable intensity level. The speech discrimination score is the percentage of words correctly identified. A Tympanometry test that creates variations of air pressure in the ear canal enables the condition of the middle ear and mobility of the eardrum to be examined. Other hearing tests may be employed and would be familiar to those skilled in the art.

In various embodiments, the methods of the present invention comprise administering a composition or formulation as disclosed elsewhere herein to a subject to increase, induce, or promote sensory hair cell regeneration in the subject. The amount of composition administered to the subject can be an effective amount, such as a prophylactically or therapeutically effective amount. An "effective amount" refers to an amount effective, at dosages and for periods of time necessary, to achieve the desired therapeutic or prophylactic result.

A "therapeutically effective amount" may vary according to factors such as the disease state, age, sex, and weight of the subject, and the ability of active agents in the composition to elicit a desired response in the subject. A therapeutically effective amount is also one in which any toxic or detrimental effects of the composition are outweighed by the therapeutically beneficial effects. The term "therapeutically effective amount" refers to an amount of a composition that is effective to "treat" a disease or disorder in a mammal (e.g., a subject).

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

"Treat," "treating" or "treatment" as used herein refers to the administration of a composition or formulation to the subject, and thereby: (i) preventing the disease or condition from occurring in a subject, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition, i.e., relieving pain or discomfort without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

In particular embodiments, compositions or formulations of the invention can be used to induce, increase, or promote sensory hair cell growth and/or to increase the number of sensory hair cells. In one embodiment, the inventive compositions and formulations can increase the number of sensory hair cells in the inner ear about 2-, about 3-, about 4-, about 5-, about 6-, about 8-, or about 10-fold, or more, as compared to the number of hair cells before treatment. Such hair cell regeneration can effectively restore or establish at least a partial improvement in the subject's balance and/or ability to hear. For example, administration of an agent can improve hearing loss and/or loss of balance by about 5, about 10, about 15, about 20, about 40, about 60, about 80, about 100% or more. Where appropriate, following treatment, the subject can be tested for an improvement in hearing or in other symptoms related to inner ear disorders. Methods for measuring hearing are well-known and include pure tone audiometry, air conduction, and bone conduction tests, as well as the tests for diagnosing hearing impairments, discussed supra. These exams measure the limits of loudness (intensity) and pitch (frequency) that a human can hear. Hearing tests include behavioral observation audiometry (for infants to seven months), visual reinforcement orientation audiometry (for children 7 months to 3 years) and play audiometry for subjects older than 3 years. Oto-acoustic emission testing can be used to test the functioning of the cochlea hair cells, and electro-cochleography provides information about the functioning of the cochlea and the first part of the nerve pathway to the brain.

In various embodiments, a method for inducing, increasing or promoting sensory hair cell regeneration in the inner ear is provided. In one embodiment, the method comprises inducing, increasing, and/or promoting proliferation of support cells by exposing the cells to a composition or formulation of the present invention at an effective concentration and for a time sufficient to increase support cell proliferation compared to support cells that are not exposed to the compositions or formulations. The invention further contemplates administering compositions or formulations of the invention to the inner ear of a subject, in an amount effective and for a time sufficient to induce, increase, and/or promote dedifferentiation and/or proliferation of support cells exposed to the compositions or formulations of the invention, compared to support cells that are not exposed to the compositions or formulations.

In certain embodiments, exposing support cells of the inner ear to compositions or formulations of the present invention induces, increases, and/or promotes proliferation of support cells, but also enhances or promotes subsequent differentiation of the proliferated hair cells into sensory hair cells compared to support cells that are not exposed to the compositions or formulations. The invention further contemplates, administering compositions or formulations of the invention to the inner ear of a subject, in an amount effective and for a time sufficient to induce, increase, and/or promote dedifferentiation and/or proliferation of support cells exposed to the compositions or formulations of the invention and/or subsequent differentiation of the proliferated and/or dedifferentiated hair cells into sensory hair cells, compared to support cells that are not exposed to the compositions or formulations.

The present invention further contemplates that the compositions and formulations disclosed herein may be administered to a subject having partial or complete hearing loss or loss of balance, to ameliorate, prevent, or treat at least one symptom associated therewith, e.g., loss of support cells and/or sensory hair cells in the cochlea and/or vestibular organs. In particular embodiments, compositions or formulations of the invention are administered in an amount effective and for a time sufficient to partially or completely restore hearing or balance in the subject compared to hearing and balance in the subject prior to administration of the compositions or formulations. In certain embodiments, compositions or formulations of the invention are administered in an amount effective and for a time sufficient to increase regeneration of sensory hair cells the subject compared to the number of sensory hair cells in the subject prior to administration of the compositions or formulations, thereby ameliorating, preventing, or treating at least one symptom associated with hearing loss or loss of balance in the subject.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following Examples 1-4 illustrate ellipticine derivatives of this invention, i.e., compound of structure (I):

Structure (I)

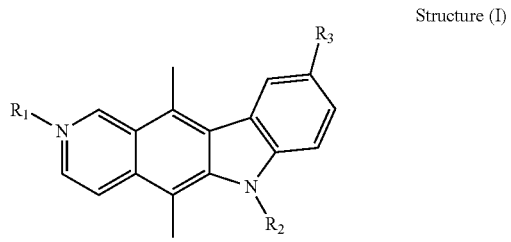

wherein $R_1$, $R_2$, $R_3$, $R_4$, $R_5$, and $R_6$ are as defined above. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., *Advanced Organic Chemistry: Reactions, Mechanisms, and Structure,* 5th edition (Wiley, December 2000)) or prepared as described in this invention.

Examples 5 and 6 describe experiments showing that ellipticine derivatives of the invention decrease p27 protein levels in cancer cells and cochlear explants, and increase cell proliferation in cochlear explants.

The following examples are provided by way of illustration only and not by way of limitation. Those of skill in the art will readily recognize a variety of noncritical parameters that could be changed or modified to yield essentially similar results.

Example 1

Iodo Methyl Ellipticinium

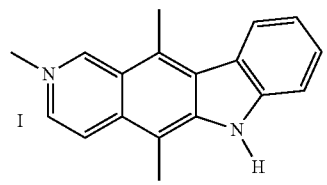

The molecule can be synthesized from ellipticine and iodomethane using the protocol described in *J. Med. Chem,* 1994, 37, 2190.

Example 2

Bromo Benzyl Ellipticinium

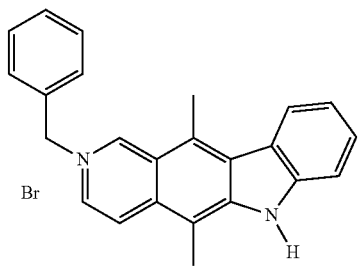

The molecule can be synthesized from ellipticine and benzyl bromide using the protocol described in *J. Med. Chem,* 1994, 37, 2190.

Example 3

Bromo Methoxy Ethyl Ellipticinium

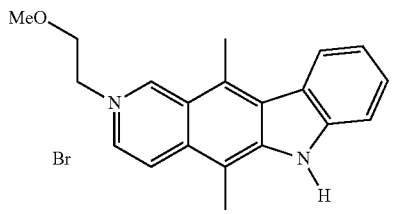

The molecule can be synthesized from ellipticine and 1-bromo 2-methoxy ethane using the protocol described in *J. Med. Chem,* 1994, 37, 2190.

Example 4

Bromo Ethyl Acetyl Ellipticinium

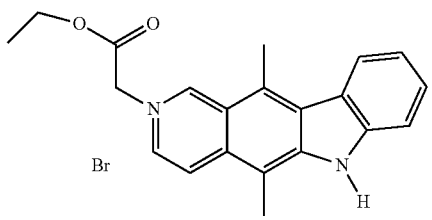

The molecule can be synthesized from ellipticine and ethyl bromo acetate using the protocol described in *J. Med. Chem*, 1994, 37, 2190.

Example 5

Ellipticine Derivatives Decrease P27 Protein Levels in U87 Cancer Cells

U87 cancer cells were cultured to sub-confluence and treated for 24 or 48 hours with i) DMSO or ii) ellipticine derivatives dissolved in DMSO. U87 cell extracts were analyzed by western blotting. Detergent-solubilized extracts were electrophoresed on a polyacrylamide gel, and the separated denatured proteins were transferred to a PVDF membrane. Antibodies to p27, p57, and the loading protein control, beta-actin, were used with infrared dye-conjugated secondary antibodies and quantified by fluorescence. Levels of 27, p57, were normalized to the beta-actin signal before comparing treated and control samples.

Figure 2:
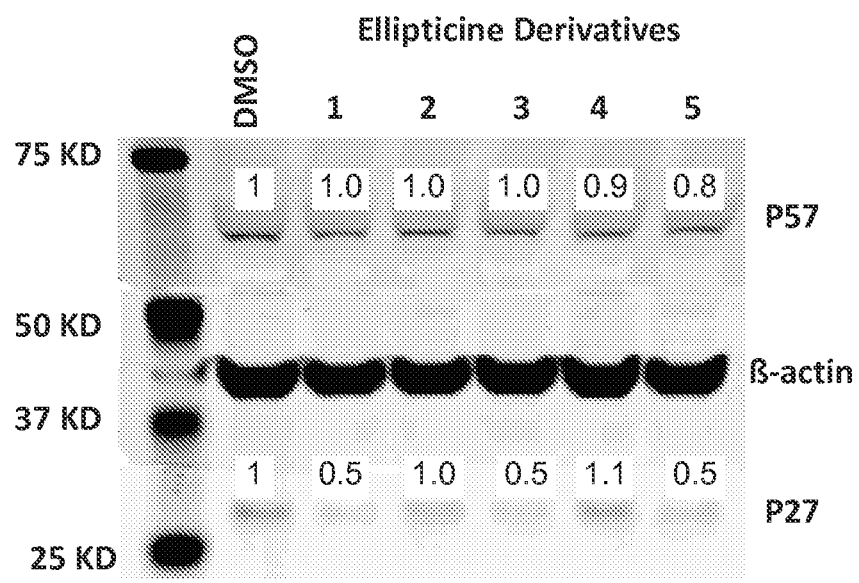
FIG. 2 shows the effect of ellipticine derivatives on p27 protein levels in U87 cancer cells in a representative western blot. U87 cancer cells were treated with the indicated ellipticine derivatives and the treatment effect on p27 protein levels in the cells was measured by western blot.

Ellipticine derivatives reduced p27 protein levels in the U87 cells (FIG. 2).

Example 6

Ellipticine Derivatives Decrease P27 Protein Levels and Increase Cell Proliferation in Cochlear Explants Postnatal day 5 rat cochlea were collected and cultured in triplicate for 24 or 48 hours with DMSO or ellipticine derivatives dissolved in DMSO.

Cochlear explant extracts were analyzed by western blotting. Detergent-solubilized extracts were electrophoresed on a polyacrylamide gel, and the separated denatured proteins transferred to a PVDF membrane. Antibodies to p27, p57, phospho-Histone H3, Pan-Histone H3 and the loading protein control, beta-actin, were used with infrared dye-conjugated secondary antibodies and quantified by fluorescence. Levels of 27, p57, phospho-Histone H3 and Pan-Histone H3 were normalized to the beta-actin signal before comparing treated and control samples.

Figure 3:
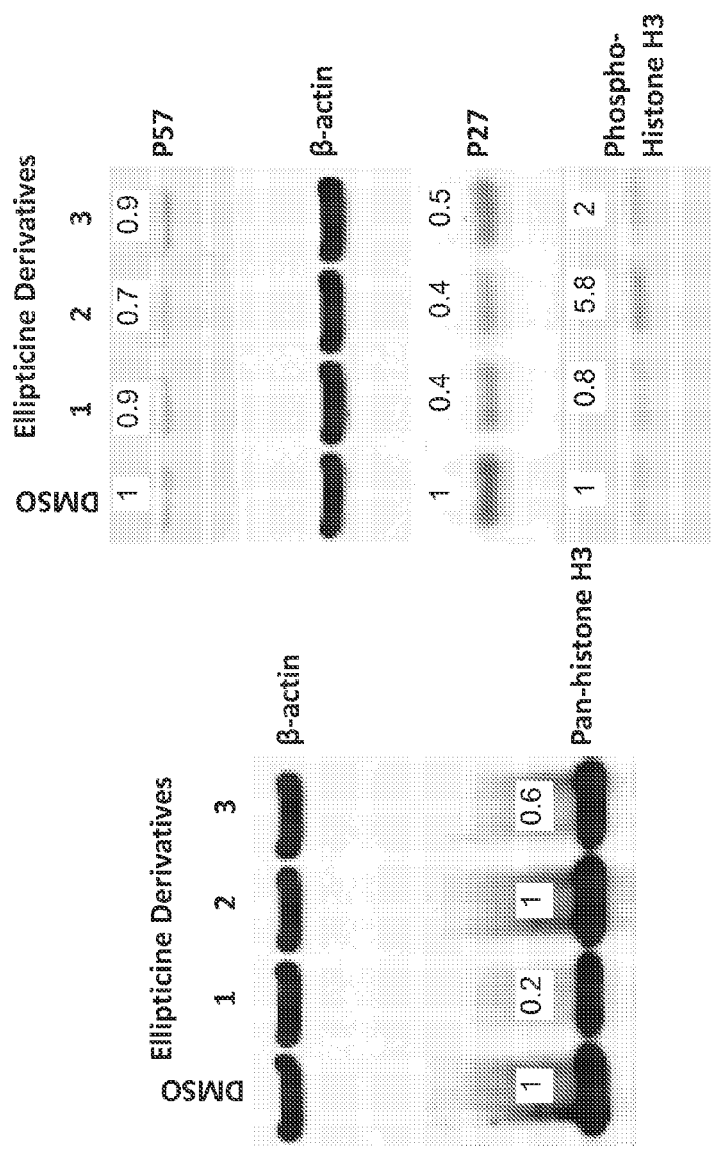
FIG. 3 shows the effect of ellipticine derivatives on p27 protein levels and phosphorylated histone H3 levels in cochlear explants in a representative western blot experiment. Cochlear explants were treated with the indicated ellipticine derivatives and the treatment effect on p27 protein levels and phosphorylated histone H3 levels in the cells were measured by western blot.

Ellipticine derivatives both reduced p27 protein levels and increased cell proliferation in the cochlear explants when compared to cochlear explants treated with vehicle (DMSO) (FIG. 3).

Example 7

Ellipticine Derivatives Decreases P27 Protein Levels and Increases Cell Proliferation 1N Hair Cell-Damaged Cochlear Explants Postnatal day 5 rat cochlea were collected and cultured with 1 mM tobramycin for two days to kill hair cells. Cultures were then treated with 3 uM bromo benzyl ellipticinium dissolved in DMSO or DMSO alone (negative control) for 24 hours.

Cochlear explant extracts were analyzed by western blotting. Detergent-solubilized extracts were electrophoresed on a polyacrylamide gel, and the separated denatured proteins transferred to a PVDF membrane. Antibodies to p27, p57, phosphorylated Histone H3, phosphorylated p130 and the house-keeping gene, β-actin were used with infrared dye-conjugated secondary antibodies and quantified by fluorescence. Levels of p27, p57, phosphorylated Histone H3, and phosphorylated p130 were normalized to the beta-actin signal before comparing treated and control samples.

Figure 4:
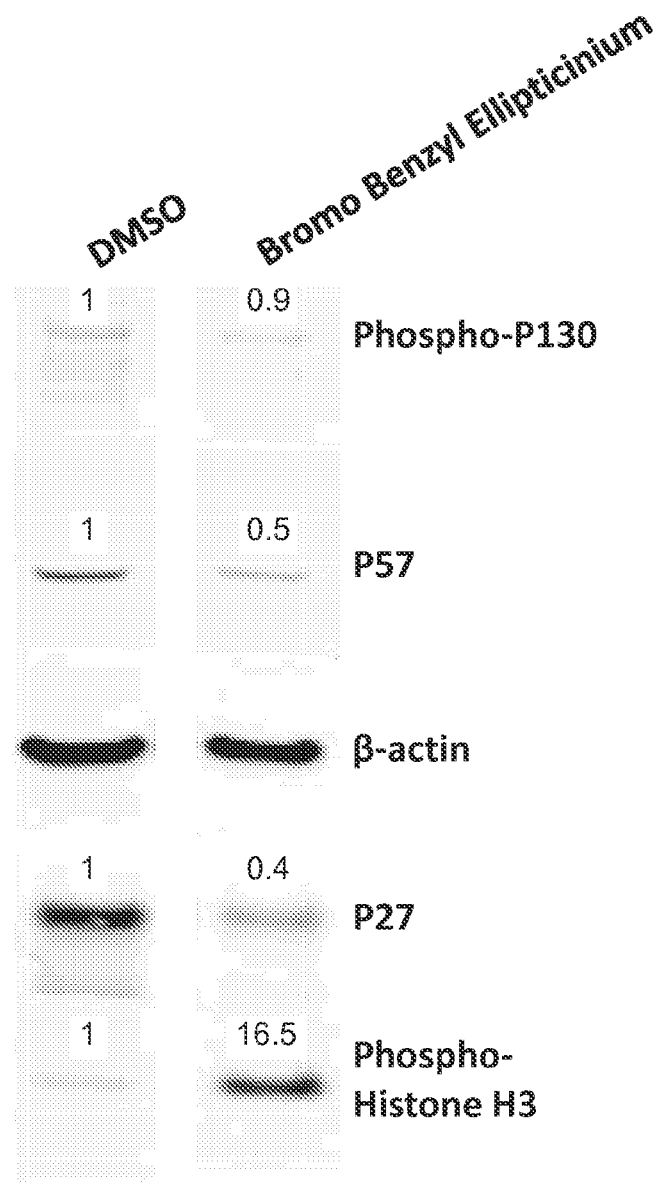
FIG. 4 shows the effect of ellipticine derivatives on p27 protein levels and phosphorylated histone H3 levels in hair cell-damaged cochlear explants in a representative western blot experiment. Cochlear explants were treated with tobramycin then with the indicated ellipticine derivatives. The treatment effect on p27 protein levels and phosphorylated histone H3 levels in the cells were measured by western blot.

Bromo benzyl ellipticinium reduced p27 protein levels and increased cell proliferation in the hair cell-damaged cochlear explants when compared to cochlear explants treated with vehicle (DMSO) (FIG. 4).

Example 8

Ellipticinium Derivatives and Gsk-3 Inhibitors Synergistically Increase Cell Proliferation in Hair Cell-Damaged Cochlear/Modiolus Explants Postnatal day 5 rat cochlea cochlea/modiolus explants were collected and cultured with 1 mM tobramycin for three days to kill hair cells. Cultures were then treated for three days with DMSO, 3 uM bromo benzyl ellipticinium, 60 uM CHIR99021, or both. Tissues were fixed with 4% paraformaldehyde, and cochlea were removed from surrounding tissue and immunostained with anti-SOX2 and anti-BrdU antibodies. Whole mount confocal microscopy was used to identify proliferating supporting cells (Brdu+/Sox2+) counted in 300 um of the basal-most cochlea. Cochlea were analyzed in triplicates per treatment group. Table 1 shows that bromo benzyl ellipticinium and CHIR99021 synergistically increase proliferation of basal cochlear cells.

TABLE 1

| Treatment | BrdU+/Sox2+ ells/300 μm of Basal Cochlea (Mean ± SD, n = 3) |
|---|---|
| DMSO negative control | 0 ± 1 |
| 3 μM bromo benzyl ellipticinium | 0 ± 0 |
| 60 μM CHIR99021 | 0 ± 0 |
| 3 μM bromo benzyl ellipticinium + 60 μM CHIR99021 | 15 ± 6 |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A composition comprising a compound of Structure I:

Structure (I)

wherein $R_1$ is hydrogen, alkyl, cycloalkyl, cycloalkylalkyl, aryl, aralkyl, heterocyclyl, heterocyclylalkyl, heteroaryl or heteroarylalkyl, wherein $R_1$ is optionally substituted with one or more $R_4$;

$R_2$ and $R_3$ are each hydrogen;

each $R_4$ is independently hydrogen, alkyl, cycloalkyl, aryl, heterocyclyl, heteroaryl, —$OR_5$, —CN, —$N_3$, —$NR_5R_6$, —C(=O)$NR_5R_6$, —$NR_5$C(=O)$R_6$, —C(=O)$OR_6$, —$SR_5$, —$SOR_5$, —$SO_2R_5$, —$NR_5$C(=O)$OR_6$, —$NR_5$C(=O)$NR_5R_6$, —O(C=O)$R_5$, —O(C=O)$NR_5$, —$NR_5SO_2R_6$; and $R_5$ and $R_6$ are each independently hydrogen, alkyl, cycloalkyl, aryl, heterocyclyl or heteroaryl; or a pharmaceutically acceptable salt, solvate, stereoisomer, racemate, or tautomer thereof and a GSK-3 inhibitor, wherein contacting a cell with the compound decreases an amount of p27 polypeptide and/or increases an amount of phosphorylated H3 polypeptide in the cell.

2. The composition of claim 1, $R_1$ is selected from the group consisting of methyl, benzyl, 2-methoxy ethyl, and ethyl acetate.

3. The composition of claim 1, wherein the GSK-3 inhibitor is selected from CHIR99021, 1-Azakenpaullone, and (2'Z,3'E)-6-Bromoindirubin-3'-oxime (BIO).

4. A method for promoting sensory hair cell regeneration comprising administering to a subject, in an amount effective to increase sensory hair cells in the subject, a composition comprising a compound of Structure I:

Structure (I)

wherein $R_1$ is hydrogen, alkyl, cycloalkyl, cycloalkylalkyl, aryl, aralkyl, heterocyclyl, heterocyclylalkyl, heteroaryl or heteroarylalkyl, wherein $R_1$ is optionally substituted with one or more $R_4$;

$R_2$ and $R_3$ are each hydrogen;

each $R_4$ is, independently hydrogen, alkyl, cycloalky, aryl, heterocyclyl, heteroaryl, —$OR_5$, —CN, —$N_3$, —$NR_5R_6$, —C(=O)$NR_5R_6$, —$NR_5$C(=O)$R_6$, —C(=O)$OR_6$, —$SR_5$, —$SOR_5$, —$SO_2R_5$, —$NR_5$C(=O)$OR_6$, —$NR_5$C(=O)$NR_5R_6$, —O(C=O)$R_5$, —O(C=O)$NR_5$, or —$NR_5SO_2R_6$; and $R_5$ and $R_6$ are each independently hydrogen, alkyl, cycloalkyl, aryl, heterocyclyl or heteroaryl; or a pharmaceutically acceptable salt, solvate, stereoisomer, racemate, or tautomer thereof, wherein contacting a cell with the compound decreases an amount of p27 polypeptide and/or increases an amount of phosphorylated H3 polypeptide in the cell, thereby promoting sensory hair cell regeneration in the subject.

5. The method of claim 4, wherein the subject has a partial or complete loss of hearing or balance.

6. The method of claim 4, wherein the subject has sensorineural hearing loss due to acute or chronic exposure to ototoxic compounds, acute or chronic exposure to noise, age related hearing loss, a genetic related hearing loss, or has auditory neuropathy.

7. The method of claim 4, wherein the subject is at risk of developing sensorineural hearing loss or auditory neuropathy.

8. The method of claim 4, wherein $R_1$ is selected from the group consisting of methyl, benzyl, 2-methoxy ethyl, and ethyl acetate.

9. The method of claim 4, wherein the composition comprises one or more small molecules that increase the gene expression of Atoh 1.

10. The method of claim 4, wherein the composition comprises one or more small molecules that increase the protein expression of Atoh 1.

11. The method of claim 4, wherein the composition comprises one or more small molecules that increase the activity of Atoh 1 protein.

12. The method of any one of claims 9 to 11, wherein the one or more small molecules that increase gene expression of Atoh 1, increase protein expression of Atoh 1, or increase the activity of Atoh 1 protein is selected from the group consisting of:

CHIR99021, 1-Azakenpaullone, and (2'Z,3'E)-6-Bromoindirubin-3'-oxime (BIO).

13. The method of claim 4, wherein the composition comprises a biodegradable polymer.

14. The method of claim 4, wherein the composition is administered to a middle ear of the subject.

15. The method of claim 14, wherein the composition is administered onto or adjacent to a round window membrane.

16. The method of claim 4, wherein the composition is administered to an inner ear of the subject.

17. The method of claim 16, wherein the composition is administered to a cochlea of the subject.

18. The method of claim 17, wherein the composition is administered to an Organ of Corti of the subject.

19. The method of claim 4, wherein the composition is administered by transtympanic administration.

20. The method of claim 4, wherein the composition is administered by transtympanic wick.

21. The method of claim 4, wherein the composition is administered by transtympanic catheter.

22. The method of claim 4, wherein the composition is administered by intracochlear injection.

* * * * *